(12) United States Patent
Buzzi

(10) Patent No.: US 12,383,590 B2
(45) Date of Patent: Aug. 12, 2025

(54) PHARMACEUTICAL DELIVERY COMPOSITIONS AND USES THEREOF

(71) Applicant: INNOVACORIUM, INC., Gainesville, FL (US)

(72) Inventor: Marcelo Buzzi, Gainesville, FL (US)

(73) Assignee: INNOVACORIUM, INC., Gainesville, FL (US)

( * ) Notice: Subject to any disclaimer, the term of this patent is extended or adjusted under 35 U.S.C. 154(b) by 162 days.

(21) Appl. No.: 17/421,978

(22) PCT Filed: Jan. 10, 2020

(86) PCT No.: PCT/US2020/013118
§ 371 (c)(1),
(2) Date: Jul. 9, 2021

(87) PCT Pub. No.: WO2020/146752
PCT Pub. Date: Jul. 16, 2020

(65) Prior Publication Data
US 2022/0118035 A1    Apr. 21, 2022

Related U.S. Application Data

(60) Provisional application No. 62/791,005, filed on Jan. 10, 2019.

(51) Int. Cl.
*A61K 36/05*     (2006.01)
*A61K 8/19*      (2006.01)
(Continued)

(52) U.S. Cl.
CPC .............. *A61K 36/05* (2013.01); *A61K 9/006* (2013.01); *A61K 9/08* (2013.01); *A61K 31/05* (2013.01);
(Continued)

(58) Field of Classification Search
CPC .......... A61K 36/05; A61K 9/006; A61K 9/08; A61K 31/05; A61K 31/07; A61K 31/192;
(Continued)

(56) References Cited

U.S. PATENT DOCUMENTS 10,149,816 B2    12/2018   Levy
2009/0169489 A1   7/2009   Haley
(Continued)

FOREIGN PATENT DOCUMENTS

CN    1226816 A      8/1999
CN    111032059 A    4/2020
(Continued)

OTHER PUBLICATIONS

Bennison LR, "The pH of wounds during healing and infection: a descriptive literature review", Wound Practice and Research, vol. 25, No. 2, Jun. 2017, pp. 65-69 (Year: 2017).*
(Continued)

*Primary Examiner* — Kyung S Chang
(74) *Attorney, Agent, or Firm* — Wolf, Greenfield & Sacks, P.C.

(57) ABSTRACT

In some aspects, the disclosure relates to compositions and methods for skin repair and regeneration. In some embodiments, compositions described by the disclosure comprise natural products (e.g., extracts) combined with biotechnological excipient systems, such as bio surfactants, suitable for the repair of compromised skin, such as mucosal tissue (e.g., oral mucosal tissue).

15 Claims, 8 Drawing Sheets

(51) Int. Cl.

| | | |
|---|---|---|
| *A61K 8/34* | (2006.01) | |
| *A61K 8/60* | (2006.01) | |
| *A61K 8/64* | (2006.01) | |
| *A61K 8/67* | (2006.01) | |
| *A61K 8/73* | (2006.01) | |
| *A61K 9/00* | (2006.01) | |
| *A61K 9/08* | (2006.01) | |
| *A61K 31/05* | (2006.01) | |
| *A61K 31/07* | (2006.01) | |
| *A61K 31/192* | (2006.01) | |
| *A61K 31/197* | (2006.01) | |
| *A61K 31/353* | (2006.01) | |
| *A61K 31/365* | (2006.01) | |
| *A61K 31/714* | (2006.01) | |
| *A61K 36/53* | (2006.01) | |
| *A61K 36/886* | (2006.01) | |
| *A61K 47/02* | (2006.01) | |
| *A61K 47/10* | (2017.01) | |
| *A61K 47/26* | (2006.01) | |
| *A61K 47/42* | (2017.01) | |
| *A61P 17/02* | (2006.01) | |
| *A61P 31/04* | (2006.01) | |

(52) U.S. Cl.
CPC ............ *A61K 31/07* (2013.01); *A61K 31/192* (2013.01); *A61K 31/197* (2013.01); *A61K 31/353* (2013.01); *A61K 31/365* (2013.01); *A61K 31/714* (2013.01); *A61K 36/53* (2013.01); *A61K 36/886* (2013.01); *A61K 47/02* (2013.01); *A61K 47/10* (2013.01); *A61K 47/26* (2013.01); *A61K 47/42* (2013.01); *A61P 17/02* (2018.01); *A61P 31/04* (2018.01)

(58) Field of Classification Search
CPC .. A61K 31/197; A61K 31/353; A61K 31/365; A61K 31/714; A61K 36/53; A61K 36/886; A61K 47/02; A61K 47/10; A61K 47/26; A61K 47/42; A61K 8/19; A61K 8/347; A61K 8/602; A61K 8/64; A61K 8/678; A61K 8/731; A61K 8/735; A61K 8/86; A61K 8/988; A61K 9/0014; A61K 31/16; A61K 35/644; A61K 36/02; A61K 47/14; A61K 47/36; A61P 17/02; A61P 31/04; A61P 1/02; A61P 25/00; A61P 31/22; A61Q 11/00; A61Q 19/00; A61F 13/00063; A61L 15/44; A61L 2300/408; A61L 2300/41

See application file for complete search history.

(56) References Cited

U.S. PATENT DOCUMENTS

| | | | |
|---|---|---|---|
| 2010/0062067 A1* | 3/2010 | Tonge | B82Y 5/00 977/773 |
| 2018/0200320 A1* | 7/2018 | Langland | A61K 36/68 |
| 2019/0160044 A1 | 5/2019 | Zeng | |
| 2019/0259158 A1 | 8/2019 | Rimm et al. | |
| 2020/0069779 A1* | 3/2020 | Farmer | A61K 8/735 |

FOREIGN PATENT DOCUMENTS

| | | |
|---|---|---|
| EP | 3290500 A1 | 3/2018 |
| KR | 20090117081 A | 11/2009 |
| WO | WO 1998/005294 A1 | 2/1998 |
| WO | WO 2002/094300 A1 | 11/2002 |
| WO | WO 2013/163714 A1 | 11/2013 |
| WO | WO 2014/095367 A1 | 6/2014 |
| WO | WO 2017/215526 A1 | 12/2017 |
| WO | WO 2018/045966 A1 | 3/2018 |
| WO | WO 2018/065314 A1 | 4/2018 |
| WO | WO 2018/145966 A1 | 8/2018 |
| WO | WO 2018/208530 A1 | 11/2018 |
| WO | WO 2019/005962 A1 | 1/2019 |

OTHER PUBLICATIONS

International Search Report and Written Opinion for Application No. PCT/US2020/013118, mailed Mar. 17, 2020.
International Preliminary Report on Patentability for Application No. PCT/US2020/013118, mailed Jul. 22, 2021.
Agrawal et al., Acetic acid dressings: Finding the Holy Grail for infected wound management. Indian J Plast Surg. Sep.-Dec. 2017;50(3):273-280. doi: 10.4103/ijps.IJPS_245_16.
PCT/US2020/013118, Mar. 17, 2020, International Search Report and Written Opinion.
PCT/US2020/013118, Jul. 22, 2021, International Preliminary Report on Patentability.

* cited by examiner

Formulation A

| | Day 0 | Day 7 | Day 14 | Day 21 |
|---|---|---|---|---|
| Wound Area (mm$^2$) | 518.58 ± 98.19 | 244.58 ± 1.64 | 32.82 ± 10.31 | 7.49 ± 10.36 |
| % Reduction | | 52.84 | 93.67 | 98.56 |

FIG. 5A

Formulation B

| | Day 0 | Day 7 | Day 14 | Day 21 |
|---|---|---|---|---|
| Wound Area (mm$^2$) | 432.72 ± 43.49 | 227.02 ± 75.18 | 39.19 ± 42.59 | 17.95 ± 18.07 |
| % Reduction | | 47.54 | 90.94 | 95.85 |

FIG. 5B

Formulation C

| | Day 0 | Day 7 | Day 14 | Day 21 |
|---|---|---|---|---|
| Wound Area (mm²) | 554.75 ± 53.84 | 256.99 ± 38.05 | 70.29 ± 1.58 | 23.95 ± 17.55 |
| % Reduction | | 53.67 | 87.33 | 95.68 |

FIG. 5C

Formulation D

| | Day 0 | Day 7 | Day 14 | Day 21 |
|---|---|---|---|---|
| Wound Area (mm²) | 491.91 ± 95.01 | 250.92 ± 9.92 | 53.73 ± 11.43 | 20.57 ± 29.09 |
| % Reduction | | 48.99 | 89.08 | 95.82 |

FIG. 5D

Saline Solution - SAL

| | Day 0 | Day 7 | Day 14 | Day 21 |
|---|---|---|---|---|
| Wound Area (mm²) | 490.44 ± 62.73 | 217.01 ± 22.49 | 71.33 ± 23.45 | 33.09 ± 25.25 |
| % Reduction | | 55.75 | 85.46 | 93.25 |

FIG. 5E

Predicate - PG

| | Day 0 | Day 7 | Day 14 | Day 21 |
|---|---|---|---|---|
| Wound Area (mm²) | 483.03 ± 50.71 | 243.84 ± 47.83 | 31.66 ± 12.29 | 11.61 ± 12.28 |
| % Reduction | | 49.52 | 93.44 | 97.60 |

FIG. 5F

Predicate - MH

| | Day 0 | Day 7 | Day 14 | Day 21 |
|---|---|---|---|---|
| |  |  |  |  |
| | |  |  |  |
| Wound Area (mm²) | 520.76 ± 6.57 | 377.14 ± 100.87 | 94.65 ± 22.96 | 50.03 ± 52.02 |
| % Reduction | | 27.58 | 81.82 | 90.39 |

Predicate - AMG

| | Day 0 | Day 7 | Day 14 | Day 21 |
|---|---|---|---|---|
| |  |  |  |  |
| |  |  |  |  |
| Wound Area (mm²) | 409.84 ± 77.35 | 221.87 ± 2.67 | 19.78 ± 3.81 | 8.10 ± 11.36 |
| % Reduction | | 45.86 | 95.17 | 98.02 |

PHARMACEUTICAL DELIVERY COMPOSITIONS AND USES THEREOF

RELATED APPLICATIONS

This Application is a national stage filing under 35 U.S.C. § 371 of international PCT application PCT/US2020/013118, filed Jan. 10, 2020, which claims priority under 35 U.S.C. § 119(e) to U.S. provisional patent application, U.S. Ser. No. 62/791,005, filed Jan. 10, 2019, the entire contents of each of which are incorporated herein by reference.

BACKGROUND

Treatments for compromised tissue, such as skin or mucosal membranes, generally include topical or systemic administration of therapeutic agents (e.g., antibacterial drugs) combined with wound dressing and mechanical or enzymatic debridement. While these treatments are typically sufficient to promote healing of minor cuts and infections, more seriously compromised tissue, such as chronic wounds, infected skin, etc., is often not adequately addressed by such modalities. A major challenge of current methods is providing a tissue microenvironment that is both refractory to microbial growth and creates molecular conditions that promote tissue regeneration and healing.

SUMMARY

Aspects of the disclosure relate to compositions and methods useful for treating compromised skin. The disclosure is based, in part, on drug delivery compositions (systems) comprising one or more of each of the following: a surface activating agent (e.g., a surfactant), a hydration agent (e.g., hygroscopic agent), and a carbonate-based buffer that maintains the pH of the composition between about pH 7.5 and pH 9.5. Without wishing to be bound by any particular theory, when administered to compromised tissue (e.g., skin, mucosal tissue, etc.) of a subject (e.g., a human subject), compositions described by the disclosure provide a microenvironment that promotes tissue healing and regeneration by simultaneously providing 1) molecular debridement; 2) adequate hydration; and 3) anti-inflammatory and antimicrobial activity (e.g., removal of bacterial biofilm as a result of disruption of scaffold exopolymeric polysaccharide structure). In some embodiments, the properties and/or activities of compositions described by the disclosure are surprising in view of currently available wound healing compositions, which typically have pH values in a neutral (e.g., about pH 7.0) to acidic (e.g., about pH 5.0-6.0) range.

Accordingly, in some aspects, the disclosure provides a composition comprising a drug delivery system comprising a carbonate buffer solution, at least two different biosurfactants, at least one hygroscopic agent, and at least one antioxidant; and at least one bioactive agent, wherein the composition has a pH that ranges from about 7.5 to about 9.5.

In some embodiments, a carbonate buffer solution comprises one of the following ions: sodium, potassium, calcium, and magnesium. In some embodiments, a carbonate buffer solution is sodium bicarbonate buffer solution.

In some embodiments, the biosurfactants of the composition are selected from a glycolipid, lipopeptide, and polymeric biosurfactant.

In some embodiments, a glycolipid is selected from a rhamnolipid, sophorolipid, trehalolipid, cellobiolipid, mannosylerythritol lipid, and any combination thereof. In some embodiments, the biosurfactants comprise at least one rhamnolipid and at least one sophorolipid. In some embodiments, a lipopeptide is selected from a surfactin, plipastatin, bacillomycin, fengycin, subtilisin, gramicidin, polymyxin, and any combination thereof.

In some embodiments, a polymeric biosurfactant is selected from emulsan, biodispersan, liposan, mannan-lipid-protein complex, carbohydrate-lipid-protein complex, and any combination thereof.

In some embodiments, the total amount of the biosurfactants in a composition ranges from about 1.5% (w/w) to about 10% (w/w). In some embodiments, the ratio of rhamnolipid to sophorolipid in a composition ranges from about 1:9 (e.g., 1% (w/w) to 99% (w/w)) to about 9:1 (e.g., 99% (w/w) to about 1% (w/w)). In some embodiments, the ratio is about 50% to 50% (e.g., 1:1).

In some embodiments, a hygroscopic agent comprises an agent selected from a glycol polymer, glycosaminoglycan, and a cellulosic polymer. In some embodiments, a glycol polymer comprises a polyethylene glycol polymer, optionally wherein the polyethylene glycol polymer comprises between 2 polymer subunits and about 50,000 polymer subunits. In some embodiments, a glycosaminoglycan is hyaluronic acid. In some embodiments, a cellulosic polymer comprises carboxymethylcellulose or hydroxyethylcellulose. In some embodiments, the amount of the hygroscopic agent in the composition ranges from about 1% (w/w) to about 10% (w/w).

In some embodiments, at least one antioxidant of the composition is a lipophilic antioxidant. In some embodiments, a lipophilic antioxidant, is Butylated Hydroxytoluene (BHT), Butylated Hydroxyanisole (BHA), and/or a tocopherol. In some embodiments, a tocopherol is alpha-tocopherol.

In some embodiments a composition comprises at least one bioactive agent. In some embodiments, a bioactive agent is a small molecule, protein, nucleic acid, or a bioactive extract.

In some embodiments, a bioactive extract is obtained (e.g., extracted) from one or more types of propolis (e.g., a propolis mixture). In some embodiments, a propolis (e.g., propolis mixture) comprises green propolis, brown propolis, red propolis, or a combination thereof (e.g., green and brown propolis, red, green and brown propolis, etc.). In some embodiments, a natural bioactive extract (e.g., a propolis extract) comprises one or more of the following: a flavonoid, artepillin C, triterpenoid, isoflavonid, and aromatic acid. In some embodiments, the ratio of green propolis to brown propolis in a composition ranges from about 1:9 to about 9:1. In some embodiments, the total amount of propolis bioactive extract in a composition ranges from about 5% (w/w) to about 20% (w/w).

In some embodiments, a bioactive natural extract is obtained (e.g., extracted) from one or more types of marine algae (e.g., a marine algae mixture). In some embodiments, one or more types of marine algae are selected from genus *Enteromorpha, Ulva, Monostroma, Codium, Caulerpa, Bryopsis, Porphyra*, and *Laminaria*. In some embodiments, a bioactive natural extract (e.g., a marine algae extract) comprises one or more sulfated polysaccharides. In some embodiments, one or more sulfated polysaccharides is selected from carrageenan, galactan, ulvan and fucoidan. In some embodiments, the bioactive extract further comprises Aloe vera extract. In some embodiments, the total amount of marine algae bioactive extract in a composition ranges from about 5% (w/w) to about 20% (w/w).

In some embodiments, a bioactive natural extract comprises one or more carotenoids and/or Vitamin A (or a derivative thereof). In some embodiments, a bioactive extract comprising carotenoids is obtained (e.g., extracted) from carrot oil. In some embodiments, a carrot oil bioactive natural extract comprises one or more B vitamin complexes. In some embodiments, one or more B vitamin complexes is a derivative of pantothenic acid or a derivative or analogue thereof. In some embodiments, a B vitamin complex comprises dexpanthenol. In some embodiments, the total amount of carrot oil bioactive natural extract in a composition ranges from about 1% (w/w) and about 5% (w/w).

In some embodiments, a composition further comprises one or more proteins (e.g., animal proteins, extracellular matrix proteins, etc.). In some embodiments, the protein comprises collagen, albumin, or a combination thereof.

In some embodiments, a bioactive natural extract is obtained (e.g., extracted) from a plant. In some embodiments, a bioactive natural extract is obtained (e.g., extracted) from *Melissa officinalis*. In some embodiments, a *Melissa officinalis* bioactive natural extract comprises one or more B vitamin complexes. In some embodiments, one or more B vitamin complexes comprise methylcobalamin and/or cyanocobalamin. In some embodiments, one or more B vitamin complexes is a derivative of pantothenic acid or a derivative or analogue thereof, optionally wherein the B vitamin complex comprises dexpanthenol. In some embodiments, the total amount of *Melissa officinalis* bioactive natural extract in a composition ranges from about 1% (w/w) to about 5% (w/w).

In some embodiments, a composition as described by the disclosure is formulated as a solid (e.g., powder, such as a lyophilized powder), liquid, gel (e.g., a hydrogel), or foam. In some embodiments, a liquid is a mouthwash. In some embodiments, a gel or foam is formulated as an aerosolized spray or a hydrogel. In some embodiments, a composition as described by the disclosure is present on or in a solid substrate. In some embodiments, a solid substrate comprises cotton fibers. In some embodiments, a solid substrate is a bandage or a cotton mask.

In some embodiments, the disclosure provides a solid substrate comprising a composition as described herein. In some embodiments, a kit further comprising one or more elastic bandages. In some embodiments, the composition is formulated as a foam, gel or liquid.

In some embodiments, a solid substrate comprises cotton fibers. In some embodiments, a solid substrate is a bandage (e.g., a non-adhesive bandage) or a mask (e.g., a cotton face mask).

In some aspects, the disclosure provides a kit comprising a composition as described herein; and, a non-adherent wound dressing. In some embodiments, a non-adherent wound dressing comprises cotton fibers.

In some aspects, the disclosure provides a kit comprising a composition as described herein; and, one or more antiviral agents effective for treating a herpes simplex virus.

In some embodiments, one or more antiviral agents is selected from acyclovir, valacyclovir and famciclovir. In some embodiments, the herpes simplex virus is Herpes simplex labialis (HSL). In some embodiments, the composition, the antiviral agent, or a combination thereof is formulated for topical administration.

In some aspects, the disclosure provides a method for treating oral cavity lesions in a subject (e.g., a human subject), the method comprising administering a composition as described herein to a subject having one or more oral cavity lesions.

In some embodiments, a subject has or is suspected of having mucositis. In some embodiments, a subject has been previously administered a chemotherapy, radiotherapy, or a combination of chemotherapy and radiotherapy. In some embodiments, a subject has undergone buco-maxillofacial surgery.

In some embodiments, the composition is administered directly to the oral cavity of the subject. In some embodiments, the administration is by oral spray or mouthwash. In some embodiments, a subject is administered the composition more than once per day (e.g., 2, 3, 4, or more times per day). In some embodiments, the composition is administered to the subject before a meal, after a meal, or both before and after a meal. In some embodiments, administration of the composition inhibits bacterial biofilm formation and/or growth.

In some aspects, the disclosure provides a method comprising administering a composition as described herein to the skin of a subject in need thereof.

In some embodiments, the skin of the subject has been subjected to a cosmetic procedure. In some embodiments, the cosmetic procedure is laser skin peeling.

In some embodiments, the skin of the subject is compromised. In some embodiments, the compromised skin is a wound (e.g., surgical incision, etc.), ulcer, or blister.

In some embodiments, administering comprises contacting the skin of the subject with a solid substrate comprising the composition. In some embodiments, the solid substrate is a non-adhesive bandage or a cotton face mask.

In some embodiments, the composition is administered topically. In some embodiments, administration occurs at least 1, 2, 3, 4, 5, 6, 7, 8, 9, or 10 times per day. In some embodiments, administration occurs at least 1, 2, 3, 4, 5, 6, 7, 8, 9, or 10 times per week.

In some embodiments, a subject has or is suspected of having diabetes (e.g., type 1 diabetes or type II diabetes). In some embodiments, the subject has a chronic wound resulting from diabetes or compromised skin resulting from insufficient blood flow, for example varicose veins or a bedsore. In some embodiments, the subject has or is suspected of having a diabetic ulcer, for example a diabetic foot ulcer.

In some embodiments, a subject has or is suspected of being infected with a Herpes simplex virus. In some embodiments, the virus is Herpes simplex labialis.

In some aspects, the disclosure provides a method of regenerating a peripheral nerve ending in a subject in need thereof, the method comprising administering to the subject: a first composition comprising a *Melissa officinalis* bioactive extract; and a second composition comprising methylcobalamin and/or cyanocobalamin.

In some embodiments, the first composition and second composition are administered as a single composition. In some embodiments, the first and/or second composition is administered topically.

In some embodiments, the skin of the subject is compromised. In some embodiments, the compromised skin is a wound, ulcer, or blister. In some embodiments, the subject has or is suspected of being infected with a Herpes simplex virus. In some embodiments, the Herpes simplex virus is Herpes simplex labialis.

BRIEF DESCRIPTION OF THE DRAWINGS

FIGS. 5A-5H are photographs depicting the healing process of full thickness excisional wounds on pig skin with various treatment and control. FIG. 5A shows data for Formulation A.

FIG. 5B shows data for Formulation B. FIG. 5C shows data for Formulation C. FIG. 5D shows data for Formulation D. FIG. 5E shows data for saline control (SAL). FIG. 5F shows data for Plurogel. FIG. 5G shows data for Medihoney. FIG. 5H shows data for Amerigel.

DETAILED DESCRIPTION

Figure 1:
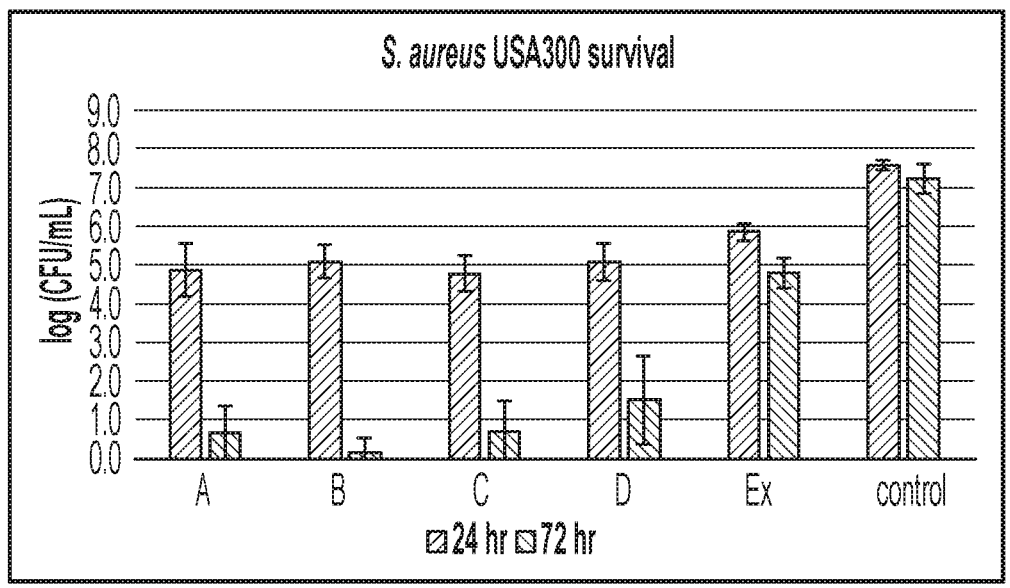
FIG. 1 shows representative data for efficacy of tissue repair formulations against 3-day-old *S. aureus* MRSA biofilms. Both daily and single applications were evaluated. Note that the data are presented as microbial survivors. Ex=excipient.

Chronic wounds that fail to progress through the normal pattern of wound healing but rather remain in a state of chronic inflammation is usually is a protease rich and pro-oxidant hostile microenvironment. Such microenvironment usually promotes degradation of growth factors and over-production of reactive oxygen species (ROS) resulting in more tissue damage and more delayed tissue repair. Microbes present in the wound also contribute to impaired tissue repair.

The disclosure relates to drug delivery systems and compositions of drugs for promoting wound healing and tissue generation. The disclosure is based, in part, on drug delivery compositions (systems) comprising one or more of each of the following: a surface activating agent (e.g., a surfactant), a hydration agent (e.g., hygroscopic agent), and a carbonate-based buffer that maintains the pH of the composition between about pH 8.0 and pH 9.5. In some embodiments, a composition further comprises one or more at least one bioactive agent.

Without wishing to be bound by any particular theory, when administered to compromised tissue (e.g., skin, mucosal tissue, etc.) of a subject, compositions described by the disclosure provide a microenvironment that promotes tissue healing and regeneration by simultaneously providing 1) molecular debridement; 2) adequate hydration; and 3) anti-inflammatory and antimicrobial activity. For example, in some embodiments, compositions described by the disclosure promote removal of bacterial biofilm as a result of disruption of scaffold exopolymeric polysaccharide structure. In some embodiments, the properties and/or activities of compositions described by the disclosure are surprising in view of currently available wound healing compositions, which typically have pH values in a neutral (e.g., about pH 7) to acidic (e.g., about pH 5.0-6.0) range.

Accordingly, in some aspects, the disclosure provides a composition comprising a drug delivery system comprising a carbonate buffer solution, at least two different biosurfactants, at least one hygroscopic agent, and at least one antioxidant; and at least one bioactive agent, wherein the composition has a pH that ranges from about 8.0 to about 9.5.

Surface Tension Adjusting Agents

The disclosure relates, in part, to compositions comprising one or more surface tension adjusting agents. In some embodiments, a surface tension adjusting agent is a surfactant.

Generally, a composition as described herein may comprise one or more surfactants (e.g., 1, 2, 3, 4, 5, 6, 7, 8, 9, 10, or more than 10 surfactants). In some embodiments, each surfactant of a composition is selected from a biosurfactant, anionic surfactant, zwitterionic surfactant, and non-ionic surfactant. In some embodiments, a composition as described herein lacks (e.g., does not comprise) a surfactant.

In some embodiments, at least one surfactant is a biosurfactant. As used herein, a "biosurfactant" refers to surface active biomolecules produced by microorganisms (e.g., certain bacterial cells) that reduce cellular surface tension (e.g., surface tension of cellular membranes, such as mammalian cell membranes).

Examples of biosurfactants include but are not limited to glycolipids (e.g., rhamnolipids, sophorolipids, trehalolipids, cellobiolipids, mannosylerythritol lipids, etc.), lipopeptides (e.g., surfactin, plipastatin, bacillomycin, fengycin, subtilisin, gramicidin, polymyxins, etc.), and polymeric biosurfactants (e.g., emulsan, biodispersan, liposan, mannan-lipid-protein, carbohydrate-lipid-protein, etc.). In some embodiments, a biosurfactant is selected from a glycolipid, lipopeptide, and polymeric biosurfactant.

In some embodiments, the biosurfactants in the present disclosure herein, are one or more biosurfactants selected from glycolipids. Glycolipids are carbohydrates linked to long-chain aliphatic acids or hydroxyaliphatic acids by an ester group. Examples of glycolipids include but are not limited to rhamnolipids, trehalolipids and sophorolipids. In some embodiments, glycolipids are produced by *Pseudomonas aeruginosa* bacterial cells.

As used herein, "rhamnolipid" refers to glycolipids, in which, one or two molecules of rhamnose are linked to one or two molecules of hydroxydecanoic acid. In some embodiments, a rhamnolipid is 3-[3-[(2R,3R,4R,5R,6S)-3,4,5-trihydroxy-6-methyloxan-2-yl]oxydecanoyloxy]decanoic acid, also referred to herein as "Rhamnolipid R1". As used herein, "sophorolipid" refers to glycolipids which are produced by yeasts and consist of a dimeric carbohydrate sophorose linked to a long-chain hydroxyl fatty acid by glycosidic linkage. Sophorolipids are may comprise a mixture of at least six to nine different hydrophobic sophorolipids. In some embodiments, a sophorolipid is a lactone form of the sophorolipid. In some embodiments, a sophorolipid is (E)-17-[(2R,3R,4S,5S,6R)-6-(acetyloxymethyl)-3-[(2S,3R,4S,5S,6R)-6-(acetyloxymethyl)-3,4,5-trihydroxyoxan-2-yl]oxy-4,5-dihydroxyoxan-2-yl]oxyoctadec-9-enoic acid.

In some embodiments, a composition comprises a combination of surfactants, such as a rhamnolipid and a sophorolipid (e.g., at least one rhamnolipid and at least one sophorolipid). The relative amounts (e.g., ratio) of surfactants (e.g., a rhamnolipid and a sophorolipid) in a composition may vary. In some embodiments, the ratio of a rhamnolipid to a sophorolipid ranges from about 1:9 to about 9:1 (e.g., any ratio between 1:9 and 9:1, for example 1:1, 2:8, 8:2, 7:3, 3:7, 6:4, 4:6, etc.).

The ratio or amount of biosurfactants in a composition (e.g., ratio of rhamnolipid to sophorolipid) may be measured, for example, by % weight (w/w), % volume (v/v), molar concentration, etc. relative to the total composition.

The total amount of biosurfactant in a composition may vary. In some embodiments, the total amount of biosurfactant in a composition ranges from about 0.1% (w/w) to about 8% (w/w). In some embodiments, the total amount of biosurfactant in a composition is about 0.1%, 0.2%, 0.3%, 0.4%, 0.5%, 0.6%, 0.7%, 0.8%, 0.9%, 1.0%, 1.1%, 1.2%, 1.3%, 1.4%, 1.5%, 1.6%, 1.7%, 1.8%, 1.9%, 2.0%, 2.1%, 2.2%, 2.3%, 2.4%, 2.5%, 2.6%, 2.7%, 2.8%, 2.9%, 3.0%, 3.1%, 3.2%, 3.3%, 3.4%, 3.5%, 3.6%, 3.7%, 3.8%, 3.9%, 4.0%, 4.1%, 4.2%, 4.3%, 4.4%, 4.5%, 4.6%, 4.7%, 4.8%, 4.9%, 5.0%, 5.1%, 5.2%, 5.3%, 5.4%, 5.5%, 5.6%, 5.7%, 5.8%, 5.9%, 6.0%, 6.1%, 6.2%, 6.3%, 6.4%, 6.5%, 6.6%, 6.7%, 6.8%, 6.9%, 7.0%, 7.1%, 7.2%, 7.3%, 7.4%, 7.5%, 7.6%, 7.7%, 7.8%, 7.9%, or about 8.0%. In some embodiments, a composition as described herein does not contain a biosurfactant.

In solution, depending on concentration and temperature, surfactants structurally form a spherical micelle called a 'unimer'. The micelle structure changes over time, collapsing and expanding to form a multimer. In some embodiments, unimers are configured to continually trap wound debris, creating a rinsing action. As the surfactant lowers the surface tension between the wound bed and a cleansing liquid, the cleansing liquid comes into intimate contact with the wound bed. This facilitates the separation of loose, non-viable tissue and microbial particles from the viable wound bed, which inhibits (e.g., prevents) biofilm formation and assists the eradication of older, more recalcitrant biofilms. In some embodiments, surfactants disrupt and prevent the reformation of biofilm post-debridement. In some embodiments, the presence of highly tensile biomolecules, such as the rhamnolipids and sophorolipid biosurfactants in compositions described herein, promotes a biochemical microdebridation that causes an effective disruption in the polysaccharide matrix of the bacterial biofilm and the removal of devitalized and necrotic tissues caused by the cellular damage.

In some embodiments, compositions described by the disclosure comprise one or more anionic surfactants. Examples of anionic surfactants include soaps, alkylbenzene sulfonates, alkyl sulfonates, alkyl sulfonates, alkyl sulfates, salts of fluorinated fatty acids, silicones, fatty alcohol sulfates, polyoxyethylene fatty alcohol ether sulfates, α-olefin sulfonate, polyoxyethylene fatty alcohol phosphates ether, alkyl alcohol amide, alkyl sulfonic acid acetamide, alkyl succinate sulfonate salts, amino alcohol alkylbenzene sulfonates, naphthenates, alkylphenol sulfonate and polyoxyethylene monolaurate.

The total amount of anionic surfactant in a composition may vary. In some embodiments, the total amount of anionic surfactant in a composition ranges from about 0.1% (w/w) to about 8% (w/w). In some embodiments, the total amount of biosurfactant in a composition is about 0.1%, 0.2%, 0.3%, 0.4%, 0.5%, 0.6%, 0.7%, 0.8%, 0.9%, 1.0%, 1.1%, 1.2%, 1.3%, 1.4%, 1.5%, 1.6%, 1.7%, 1.8%, 1.9%, 2.0%, 2.1%, 2.2%, 2.3%, 2.4%, 2.5%, 2.6%, 2.7%, 2.8%, 2.9%, 3.0%, 3.1%, 3.2%, 3.3%, 3.4%, 3.5%, 3.6%, 3.7%, 3.8%, 3.9%, 4.0%, 4.1%, 4.2%, 4.3%, 4.4%, 4.5%, 4.6%, 4.7%, 4.8%, 4.9%, 5.0%, 5.1%, 5.2%, 5.3%, 5.4%, 5.5%, 5.6%, 5.7%, 5.8%, 5.9%, 6.0%, 6.1%, 6.2%, 6.3%, 6.4%, 6.5%, 6.6%, 6.7%, 6.8%, 6.9%, 7.0%, 7.1%, 7.2%, 7.3%, 7.4%, 7.5%, 7.6%, 7.7%, 7.8%, 7.9%, or about 8.0%. In some embodiments, a composition as described herein lacks (e.g., does not comprise) an anionic surfactant.

In some embodiments, compositions described by the disclosure comprise one or more non-ionic surfactants. Examples of non-ionic surfactant include Polyethylene glycol alkyl ethers (Brij), Octaethylene glycol monododecyl ether, Pentaethylene glycol monododecyl ether, Polypropylene glycol alkyl ethers, Glucoside alkyl ethers, Decyl glucoside, Lauryl glucoside, Octyl glucoside, Polyethylene glycol octylphenyl ethers, Polyethylene glycol alkylphenyl ethers, Glycerol alkyl esters, Glyceryl laurate, Polyoxyethylene glycol sorbitan alkyl esters, Sorbitan alkyl esters, Cocamide MEA, cocamide DEA, Block copolymers of polyethylene glycol and polypropylene glycol: Poloxamers, Polyethoxylated tallow amine (POEA).

The total amount of non-ionic surfactants in a composition may vary. In some embodiments, the total amount of non-ionic surfactants in a composition ranges from about 0.1% (w/w) to about 8% (w/w). In some embodiments, the total amount of non-ionic surfactants in a composition is about 0.1%, 0.2%, 0.3%, 0.4%, 0.5%, 0.6%, 0.7%, 0.8%, 0.9%, 1.0%, 1.1%, 1.2%, 1.3%, 1.4%, 1.5%, 1.6%, 1.7%, 1.8%, 1.9%, 2.0%, 2.1%, 2.2%, 2.3%, 2.4%, 2.5%, 2.6%, 2.7%, 2.8%, 2.9%, 3.0%, 3.1%, 3.2%, 3.3%, 3.4%, 3.5%, 3.6%, 3.7%, 3.8%, 3.9%, 4.0%, 4.1%, 4.2%, 4.3%, 4.4%, 4.5%, 4.6%, 4.7%, 4.8%, 4.9%, 5.0%, 5.1%, 5.2%, 5.3%, 5.4%, 5.5%, 5.6%, 5.7%, 5.8%, 5.9%, 6.0%, 6.1%, 6.2%, 6.3%, 6.4%, 6.5%, 6.6%, 6.7%, 6.8%, 6.9%, 7.0%, 7.1%, 7.2%, 7.3%, 7.4%, 7.5%, 7.6%, 7.7%, 7.8%, 7.9%, or about 8.0%. In some embodiments, a composition as described herein lacks (e.g., does not comprise) a non-ionic surfactant.

A composition may also comprise one or more zwitterionic surfactants. Examples of zwitterionic surfactants include but are not limited to synthetic zwitterionic surfactants (e.g., one or more hydroxysultaines) and/or naturally occurring zwitterionic surfactants (e.g., one or more betaines, phosphatidylcholines, and/or lecithin components). In some embodiments, the zwitterionic surfactant is cocamidopropyl betaine.

The total amount of zwitterionic surfactants in a composition may vary. In some embodiments, the total amount of zwitterionic surfactants in a composition ranges from about 0.1% (w/w) to about 8% (w/w). In some embodiments, the total amount of zwitterionic surfactants in a composition is about 0.1%, 0.2%, 0.3%, 0.4%, 0.5%, 0.6%, 0.7%, 0.8%, 0.9%, 1.0%, 1.1%, 1.2%, 1.3%, 1.4%, 1.5%, 1.6%, 1.7%, 1.8%, 1.9%, 2.0%, 2.1%, 2.2%, 2.3%, 2.4%, 2.5%, 2.6%, 2.7%, 2.8%, 2.9%, 3.0%, 3.1%, 3.2%, 3.3%, 3.4%, 3.5%, 3.6%, 3.7%, 3.8%, 3.9%, 4.0%, 4.1%, 4.2%, 4.3%, 4.4%, 4.5%, 4.6%, 4.7%, 4.8%, 4.9%, 5.0%, 5.1%, 5.2%, 5.3%, 5.4%, 5.5%, 5.6%, 5.7%, 5.8%, 5.9%, 6.0%, 6.1%, 6.2%, 6.3%, 6.4%, 6.5%, 6.6%, 6.7%, 6.8%, 6.9%, 7.0%, 7.1%, 7.2%, 7.3%, 7.4%, 7.5%, 7.6%, 7.7%, 7.8%, 7.9%, or about 8.0%. In some embodiments, a composition as described herein lacks (e.g., does not comprise) a zwitterionic surfactant.

pH/Buffering Systems

Currently used skin care compositions typically have a pH that is close to the natural pH of human skin (e.g., pH 6.8-7.0) or slightly more acidic than the pH of human skin (e.g., pH 5.0-7.0). The disclosure is based, in part, on compositions having a pH that is greater than 7 (e.g., more basic or alkaline than neutral) which provide a microenvironment that promotes tissue healing and regeneration. In some embodiments, the healing and/or regenerative activity of compositions described by the disclosure is surprising in view of the more basic pH of the compositions compared to typical wound care products.

The pH of a composition as described by the disclosure ranges from about 7.5 to about 10.0. In some embodiments, the pH of a composition described by the disclosure ranges from about 8.0 to about 9.5. In some embodiments, the pH of a composition described by the disclosure is about 7.5, 7.6, 7.7, 7.8, 7.9, 8.0, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, or 10.0). Methods of measuring pH of a composition are known, for example by pH meter, electrode-based measurement (e.g., glass electrodes, reference electrodes, combination electrodes, etc.), colorimetric measurement, etc. Typically pH is measured at room temperature (e.g., between 18° C. and 24° C.). However, it should be recognized that pH may be measured at other temperatures (e.g., below 10° C., above 25° C., etc.).

The pH of a composition may be maintained by a buffering system. Examples of buffering systems include but are not limited to carbonate buffering systems, phosphate buffering systems, protein buffering systems, etc. A composition may comprise 1, 2, 3, 4, 5, 6, 7, 8, 9, 10, or more buffering systems.

The disclosure is based, in part, on compositions comprising a carbonate buffering system. Generally, a "carbonate buffering system" refers to a solution comprising a weak acid (e.g., carbonic acid) and its conjugate base (e.g., the bicarbonate anion) which buffers changes in the pH of the solution. The conjugate base (e.g., bicarbonate anion) may be provided by any conjugate salt of carbonic acid, for example sodium bicarbonate ($NaHCO_3$), potassium bicarbonate ($KHCO_3$), caesium bicarbonate ($CsHCO_3$), magnesium bicarbonate ($Mg(HCO_3)_2$), calcium bicarbonate ($Ca(HCO_3)_2$), and ammonium bicarbonate ($NH_5CO_3$). In some embodiments, a carbonate buffering system comprises sodium bicarbonate ($NaHCO_3$). In some embodiments, a carbonate buffering system comprises ammonium bicarbonate ($NH_5CO_3$). In addition to pH buffering, certain buffering systems (e.g., Na-based, and $NH_4$-based buffering systems) increase the concentration of $Na^+$ or $NH_4^+$ ions in a composition or in a microenvironment created when the composition is contacted to compromised tissue (e.g., a wound, blister, ulcer, etc.). Without wishing to be bound by any particular theory, large ions (e.g., sodium ions) bind to certain molecules on the surface of mammalian cells, such as heparin sulfate (HS), and prevent entry of pathogens into the cells, for example as described by Rabenstein et al. (2002) *Nat. Prod. Rep.* 19:312-331. In some embodiments, binding of large ions to cellular membrane also influences signal transduction of growth factors, such as FGF and EGF, which are important for skin regeneration.

In some embodiments, compositions described by the disclosure contain (or provide) an amount of ions (e.g., $Na^+$ or $NH_4^+$ ions) in a wound microenvironment that is sufficient to disrupt binding of microbes, such as bacteria and viruses, to the proteoglycans (e.g., HS, etc.) on the surface of target cells.

In some embodiments, a composition described by the disclosure comprises between about 0.5% (w/w) and about 10% (w/w) bicarbonate salt (e.g., sodium bicarbonate). In some embodiments, a composition comprises between about 2% and about 5% (w/w) bicarbonate salt (e.g., sodium bicarbonate), for example about 2%, 2.1%, 2.2%, 2.3%, 2.4%, 2.5%, 2.6%, 2.7%, 2.8%, 2.9%, 3.0%, 3.1%, 3.2%, 3.3%, 3.4%, 3.5%, 3.6%, 3.7%, 3.8%, 3.9%, 4.0, 4.1%, 4.2%, 4.3%, 4.4%, 4.5%, 4.6%, 4.7%, 4.8%, 4.9%, or 5% (w/w) sodium bicarbonate. In some embodiments, a composition as described herein lacks (e.g., does not comprise) carbonate buffering system.

Hydration Agents

Compositions of the disclosure may comprise one or more (e.g., 1, 2, 3, 4, 5, 6, 7, 8, 9, 10, or more) hydration agents. A "hydration agent" or "hygroscopic agent" generally refers to a molecule or molecules that attract and/or hold water molecules from the surrounding environment, either through absorption or adsorption. Examples of hygroscopic agents include polymers, such as cellulosic polymers, glycolic polymers, glycosaminoglycans, mucopolysaccharides, etc.

In some embodiments, a hygroscopic agent is not a deliquescent agent (e.g., a molecule that absorbs sufficient water from its surroundings so as to form an aqueous solution). Examples of deliquescent agents include salts (e.g., calcium chloride, magnesium chloride, zinc chloride, ferric chloride, carnallite, potassium carbonate, potassium phosphate, ferric ammonium citrate, ammonium nitrate, potassium hydroxide, and sodium hydroxide).

In some embodiments a composition comprises one or more cellulosic polymers, for example 1, 2, 3, 4, 5, 6, 7, 8, 9, 10, or more cellulosic polymers. In some embodiments, a composition lacks (e.g., does not comprise) a hydration agent. Generally, cellulosic polymers comprise two or more repeating subunits (e.g., polymer subunits) of glucose. Examples of cellulosic polymers include methylcellulose, hydroxymethyl cellulose, hydroxypropyl cellulose (HPC), hydroxypropyl methylcellulose (HPMC), hydroxyethyl cellulose, and carboxy methylcellulose (CMC). In some embodiments, at least one of the cellulosic polymers is hydroxyethyl cellulose or carboxy methylcellulose.

The amount of the one or more cellulosic polymers in a composition may vary. In some embodiments, a composition comprises between about 0.1% (w/w) and about 5% (w/w) cellulosic polymer. In some embodiments, a composition comprises about 0.1%, 0.2%, 0.3%, 0.4%, 0.5%, 0.6%, 0.7%, 0.8%, 0.9%, 1.0%, 1.1%, 1.2%, 1.3%, 1.4%, 1.5%, 1.6%, 1.7%, 1.8%, 1.9%, 2.0%, 2.1%, 2.2%, 2.3%, 2.4%, 2.5%, 2.6%, 2.7%, 2.8%, 2.9%, 3.0%, 3.1%, 3.2%, 3.3%, 3.4%, 3.5%, 3.6%, 3.7%, 3.8%, 3.9%, 4.0%, 4.1%, 4.2%, 4.3%, 4.4%, 4.5%, 4.6%, 4.7%, 4.8%, 4.9%, or 5.0% (w/w) cellulosic polymer.

In some embodiments a composition comprises one or more glycolic polymers, for example 1, 2, 3, 4, 5, 6, 7, 8, 9, 10, or more glycolic polymers. Generally glycolic polymers comprise two or more repeating subunits (e.g., polymer subunits) of a polyether, such as ethylene oxide. In some embodiments, the glycolic polymer is polyethylene glycol (PEG, also referred to as PEO and POE). Additional examples of glycolic polymers include methoxypoly(ethylene glycol) and polypropylene glycol (PPG). In some embodiments, at least one of the glycolic polymers is PEG.

The number of polymer subunits in a glycolic polymer (e.g., PEG) may vary. In some embodiments, a glycolic polymer (e.g., PEG) comprises between about 2 and 10,000,000 polymer subunits (e.g., any integer between 2 and 10,000,000, inclusive). In some embodiments, a glycolic polymer (e.g., PEG) comprises more than 10,000,000 polymer subunits.

In some embodiments, a glycolic polymer, such as a PEG polymer, is described by its molecular weight (e.g., as measured in g/mol). In some embodiments, a glycolic polymer is PEG 400 (e.g., PEG polymer having an average molecular weight of 400 daltons), PEG 500 (e.g., PEG polymer having an average molecular weight of 500 daltons), PEG 1000 (e.g., PEG polymer having an average molecular weight of 1000 daltons), PEG 3500 (e.g., PEG polymer having an average molecular weight of 3500 daltons), PEG 4000 (e.g., PEG polymer having an average molecular weight of 4000 daltons), PEG 10,000 (e.g., PEG polymer having an average molecular weight of 10,000 daltons), PEG 50,000 (e.g., PEG polymer having an average molecular weight of 50,000 daltons), PEG 100,000 (e.g., PEG polymer having an average molecular weight of 100,000 daltons), or PEG 1,000,000 (e.g., PEG polymer having an average molecular weight of 1,000,000 daltons).

The geometry (e.g., structure) of a glycolic polymer, such as PEG may vary. In some embodiments, a glycolic polymer is a linear polymer (e.g., linear PEG). In some embodiments, a glycolic polymer is a branched polymer (e.g., branched PEG, such as a "star PEG"). In some embodiments, a glycolic polymer is a comb PEG (e.g., multiple PEG chains grafted onto a polymer backbone).

The amount of the one or more glycolic polymer (e.g., PEG) in a composition may vary. In some embodiments, a composition comprises between about 0.1% (w/w) and about 15% (w/w) glycolic polymer. In some embodiments, a composition comprises about 0.1%, 0.2%, 0.3%, 0.4%, 0.5%, 0.6%, 0.7%, 0.8%, 0.9%, 1.0%, 1.1%, 1.2%, 1.3%, 1.4%, 1.5%, 1.6%, 1.7%, 1.8%, 1.9%, 2.0%, 2.1%, 2.2%, 2.3%, 2.4%, 2.5%, 2.6%, 2.7%, 2.8%, 2.9%, 3.0%, 3.1%, 3.2%, 3.3%, 3.4%, 3.5%, 3.6%, 3.7%, 3.8%, 3.9%, 4.0%, 4.1%, 4.2%, 4.3%, 4.4%, 4.5%, 4.6%, 4.7%, 4.8%, 4.9%, or 5.0% (w/w) glycolic polymer. In some embodiments, a composition comprises about 10%, 11%, 12%, 13%, 14%, or 15% (w/w) glycolic polymer. In some embodiments, a composition comprises no more than 15%-20% (w/w) (e.g., no more than 15%, 16%, 17%, 18%, 19%, or 20% (w/w)) glycolic polymer.

In some embodiments a composition comprises one or more glycosaminoglycans, for example 1, 2, 3, 4, 5, 6, 7, 8, 9, 10, or more glycosaminoglycans. Generally, glycosaminoglycans are long unbranched polysaccharides that comprise two or more repeating disaccharide subunits (e.g., polymer subunits), for example an amino sugar and a uronic sugar (e.g., glucuronic acid, iduronic acid) or galactose. Examples of glycosaminoglycans include heparin (Hep)/heparin sulfate (HS), chondroitin sulfate (CS)/dermatan sulfate (DS) and hyaluronic acid (HA), etc. In some embodiments, at least one of the glycosaminoglycans is hyaluronic acid (HA).

The number of polymer subunits, and consequently the molecular weight (e.g., weight average molecular weight), of hyaluronic acid (HA) may vary. In some embodiments, a hyaluronic acid (HA) comprises a molecular weight between about 5,000 to 20,000,000 daltons. In some embodiments, the number of disaccharide polymer subunits in HA ranges from about 2 polymer subunits to about 50,000 polymer subunits (e.g., any integer between 2 and 50,000, inclusive).

The amount of the one or more glycosaminoglycans in a composition may vary. In some embodiments, a composition comprises between about 0.1% (w/w) and about 5% (w/w) glycosaminoglycans. In some embodiments, a composition comprises about 0.1%, 0.2%, 0.3%, 0.4%, 0.5%, 0.6%, 0.7%, 0.8%, 0.9%, 1.0%, 1.1%, 1.2%, 1.3%, 1.4%, 1.5%, 1.6%, 1.7%, 1.8%, 1.9%, 2.0%, 2.1%, 2.2%, 2.3%, 2.4%, 2.5%, 2.6%, 2.7%, 2.8%, 2.9%, 3.0%, 3.1%, 3.2%, 3.3%, 3.4%, 3.5%, 3.6%, 3.7%, 3.8%, 3.9%, 4.0%, 4.1%, 4.2%, 4.3%, 4.4%, 4.5%, 4.6%, 4.7%, 4.8%, 4.9%, or 5.0% (w/w) glycosaminoglycans.

In some embodiments, a drug delivery composition described by the disclosure comprises water. The amount of water in a composition may vary. In some embodiments, a composition comprises at least 1%, 5%, 10%, 20%, 30%, 40%, 50%, 60%, 70%, 80%, 90%, 95%, or 99% (w/w) water.

Bioactive Agents

Compositions described by the disclosure may comprise one or more bioactive agents. Examples of bioactive agents include antimicrobial agents (e.g., antibacterial agents, antiviral agents, anti-parasitic agents, etc.), cytotoxic agents, anticancer agents, free-radical scavengers, antioxidants, receptor ligands (e.g., molecules that induce or inhibit cell signaling, etc.), etc. A bioactive agent may be a small molecule (e.g., chemical), peptide, protein, polypeptide, nucleic acid (e.g., DNA, RNA, etc.), or a bioactive extract. In some embodiments, a composition comprises 1, 2, 3, 4, 5, 6, 7, 8, 9, 10, 11, 12, 13, 14, 15, 16, 17, 18, 19, or 20 bioactive agents. In some embodiments, a composition comprises more than 20 bioactive agents.

In some embodiments, a bioactive agent is an antimicrobial agent, such as an antibacterial agent, antiviral agent, or an anti-parasitic agent. Generally, an antimicrobial agent can be a small molecule (e.g., chemical), peptide, protein, polypeptide, nucleic acid (e.g., DNA, RNA, etc.). Examples of antimicrobial agents include but are not limited to small molecules derived from bacteria and fungi (e.g., amoxicillin, doxycycline, cephalexin, ciprofloxacin, metronidazole, etc.), small molecules derived from plants (e.g., tannins, flavones, phenolics, alkaloids, etc.), and antimicrobial peptides (e.g., maxamin, dermicidin, mecropin, andropin, etc.). In some embodiments, a bioactive agent is a plant-derived antimicrobial agent, for example baicalin (e.g., extracted from *Scutellaria baicalensis* or *Scutellaria lateriflora*) or andrographolide (e.g., extracted from *Andrographis paniculata*). In some embodiments, a composition as described herein lacks a chemical or elemental antimicrobial agent, for example silver (e.g., silver-based compounds, such as silver sulfadiazine) or zinc (e.g., zinc-based compounds, such as zinc oxide).

In some embodiments, a bioactive agent is an cytotoxic agent. Examples of cytotoxic agents include but are not limited to alkylating agents (e.g., cyclophosphamide, nitrosoureas, etc.), anthracyclines (e.g., doxorubicin, daunorubicin, etc.), taxanes (e.g., taxol, paclitaxel, etc.), HDAC inhibitors, nucleotide analogues (e.g., gemcitabine, etc.), platinum-based compounds (e.g., cisplatin, etc.), and vinca alkaloids (e.g., vinblastine, etc.).

In some embodiments, a bioactive agent is an antioxidant or a free-radical scavenger. Examples of antioxidants and free-radical scavengers include but are not limited to certain enzymes (e.g., superoxide dismutase, glutathione peroxidase, glucose oxidase-catalase, etc.), carotenoids (e.g., astaxanthin, beta-carotene, tocopherol, etc.), phenolic compounds (e.g., plant-derived polyphenols, such as anthocyanins, flavan-3-ols (catechin), flavonols (e.g., quercetin and rutin), cinnamates (e.g., S-glutathionylcaftaric acid), caffeic acid phenethyl ester (CAPE), chalcones, isoflavonoids (e.g., 7-O-methylvestitol, medicarpin, and 3,4,2',3'-tetrahydrochalcone), etc.

In some embodiments, a bioactive agent is a cell-signaling molecule, such as a receptor ligand. Examples of cell-signaling molecules include but are not limited to neurotransmitters (e.g., GABA, glutamate, acetylcholine, serotonin, dopamine, etc.), cytokines (e.g., IL-4, IL-15, TNFα, IFNγ, etc.), hormones (e.g., estrogen, etc.), small molecules (e.g., nitric oxide, etc.), certain peptides (e.g., neuropeptides, growth factors, etc.), etc.

As used herein, a "bioactive extract" refers to a composition comprising one or more bioactive agents that has been extracted (e.g., isolated) from an organic source, for example one or more plants or plant products, animals or animal products, insects or insect products, microorganisms or microbial products, etc. Generally, bioactive extracts may be produced by any suitable method, for example solvent-based extraction methods (e.g., alcoholic extraction, hydrocarbon extraction, etc.), maceration extraction methods, ultrasound extraction (e.g., sonication), microwave-assisted extraction (MAE), etc. However, the skilled artisan will appreciate that an appropriate extraction method will depend upon the type of material from which the bioactive agents are sought to be isolated and will select an extraction method accordingly.

The amount of a bioactive agent or extract in a composition may vary. In some embodiments, the concentration of a bioactive agent or bioactive extract in a composition ranges from about 0% w/w (absent) to about 20% w/w (e.g., about 1%, 2%, 3%, 4%, 5%, 6%, 7%, 8%, 9%, 10%, 11%, 12%, 13%, 14%, 15%, 16%, 17%, 18%, 19%, or 20%) of the total weight of the composition.

Propolis Bioactive Extracts

In some embodiments, a composition comprises a bioactive extract obtained from propolis. "Propolis" generally refers to a resinous material produced by honey bees (e.g., Apis, and other species) that comprises a variety of chemicals and molecules, including waxes, fatty acids, pollen, aromatic oils, and certain bioactive molecules (e.g., flavonoids, isoflavinoids, chalcones, pterocarpans, etc.). Propolis can be found in several areas of the world, including North and Central America (e.g., United States, Canada, Mexico, Cuba, etc.), South America (e.g., Brazil, Colombia, Chile, etc.), Asia (e.g., China), and New Zealand. In some embodiments, a propolis bioactive extract is obtained from a blend (e.g., a mixture) comprising at least one Brazilian propolis variety. A propolis bioactive extract may be produced by any suitable extraction method, for example ethanol/glycol extraction or supercritical $CO_2$ extraction.

Characterization of propolis sources can vary. For example, Brazilian propolis was originally classified by geographic origin and/or physiochemical properties, and at least 12 propolis sources were identified, including but not limited to five in the southern Brazil group (group 3), one in the southeastern Brazil group (group 12), and six in the northeastern Brazil group (group 6). However, when classified by botanical origin, three sources of Brazilian propolis were identified for the same propolis varieties: poplar trees (e.g., *Populus* sp.), bacchariases (e.g., *Baccharis* sp., such as *Baccharis dracunculifolia*, etc.), and bushmints (e.g., *Hyptis* sp., such as *Hyptis divaricata*). Additional sources of propolis are known, for example as described by Park et al. (2002) *J. Agric. Food Chem* 50:2502-2506, and Dezmirean et al. (2017) *J. Apicultural Res* 56(5):588-597. In some embodiments, propolis is characterized by its color, for example red propolis, green propolis, brown propolis, etc.

"Red propolis" refers to a propolis that is botanically derived from plants such as *Dalbergia ecastophyllum* (*D. ecastophyllum*) (L) Taub. (Fabaceae), which are popularly known in Brazil as 'rabo-de-bugio'. In some embodiments, red propolis is obtained from a region selected from Brazil, Cuba, Mexico, China, and Nigeria. Sources of red propolis are described, for example by Corbellini Rufatto et al. (2017) *Asian Pacific Journal of Tropical Biomedicine* 7(7): 591-598.

"Green propolis" refers to a propolis that is botanically derived from plants such as *Baccharis dracunculifolia* DC (Asteraceae), for example as described by Lopes Machado et al, (2012) *Evid Based Complement Alternat Med.* 2012: 157652. In some embodiments, green propolis is obtained from Brazil (e.g., south-eastern Brazil, for example Bahia state, Minas Gerais state, Sao Paulo state, or Parana state).

Brown propolis" refers to a propolis that is botanically derived from plants such as *Populus* species (*P. alba, P. nigra, P. tremula*) or *Clusia* species. In some embodiments, brown propolis is obtained from a region selected from Brazil, Venezuela, Cuba, and Europe.

The ratio of each type of propolis in a mixture from which a propolis bioactive extract is produced can vary. For example, in some embodiments, a propolis mixture comprises green and brown propolis in a ratio ranging from about 9:1 to about 1:9 (e.g., 1:1, 1:2, 1:3, 1:4, 1:5, 1:6, 1:7, 1:8, 1:9, 2:1, 2:3, 2:4, 2:5, 2:6, 2:7, 2:8, 2:9, 3:1, 3:2, 3:4, 3:5, 3:6, 3:7, 3:8, 3:9, 4:1, 4:2, 4:3, 4:5, 4:6, 4:7, 4:8, 4:9, 5:1, 5:2, 5:3, 5:4, 5:6, 5:7, 5:8, 5:9, 6:1, 6:2, 6:3, 6:4, 6:5, 6:7, 6:8, 6:9, 7:1, 7:2, 7:3, 7:4, 7:5, 7:6, 7:8, 7:9, 8:1, 8:2, 8:3, 8:4, 8:5, 8:6, 8:7, 8:9, 9:8, 9:7, 9:6, 9:5, 9:4, 9:3, 9:2, 9:1, etc.). In some embodiments, a propolis mixture comprises green and red propolis in a ratio ranging from about 9:1 to about 1:9 (e.g., 1:1, 1:2, 1:3, 1:4, 1:5, 1:6, 1:7, 1:8, 1:9, 2:1, 2:3, 2:4, 2:5, 2:6, 2:7, 2:8, 2:9, 3:1, 3:2, 3:4, 3:5, 3:6, 3:7, 3:8, 3:9, 4:1, 4:2, 4:3, 4:5, 4:6, 4:7, 4:8, 4:9, 5:1, 5:2, 5:3, 5:4, 5:6, 5:7, 5:8, 5:9, 6:1, 6:2, 6:3, 6:4, 6:5, 6:7, 6:8, 6:9, 7:1, 7:2, 7:3, 7:4, 7:5, 7:6, 7:8, 7:9, 8:1, 8:2, 8:3, 8:4, 8:5, 8:6, 8:7, 8:9, 9:8, 9:7, 9:6, 9:5, 9:4, 9:3, 9:2, 9:1, etc.). In some embodiments, a propolis mixture comprises brown and red propolis in a ratio ranging from about 9:1 to about 1:9 (e.g., 1:1, 1:2, 1:3, 1:4, 1:5, 1:6, 1:7, 1:8, 1:9, 2:1, 2:3, 2:4, 2:5, 2:6, 2:7, 2:8, 2:9, 3:1, 3:2, 3:4, 3:5, 3:6, 3:7, 3:8, 3:9, 4:1, 4:2, 4:3, 4:5, 4:6, 4:7, 4:8, 4:9, 5:1, 5:2, 5:3, 5:4, 5:6, 5:7, 5:8, 5:9, 6:1, 6:2, 6:3, 6:4, 6:5, 6:7, 6:8, 6:9, 7:1, 7:2, 7:3, 7:4, 7:5, 7:6, 7:8, 7:9, 8:1, 8:2, 8:3, 8:4, 8:5, 8:6, 8:7, 8:9, 9:8, 9:7, 9:6, 9:5, 9:4, 9:3, 9:2, 9:1, etc.). In some embodiments, a propolis mixture comprises green, brown, and red propolis in a ratio that ranges from about 9:1:1 to about 1:9:1, to about 1:1:9 (e.g., 1:1:1, 1:2:1, 2:1:1, 1:1:2, etc.).

The amount of a propolis bioactive extract in a composition of the disclosure may vary. In some embodiments, a composition as described herein (e.g., a drug delivery composition) comprises between about 0.1% w/w and about 20% w/w of a propolis bioactive extract. In some embodiments, a composition comprises between about 0.1% w/w and about 4% w/w of propolis bioactive extract. In some embodiments, a composition comprises between about 1% and about 5% w/w of propolis bioactive extract. In some embodiments, a composition comprises between about 3% and about 7% w/w of propolis bioactive extract. In some embodiments, a composition comprises between about 5% and about 20% w/w of propolis bioactive extract.

Extracts obtained from propolis (e.g., one or more propolis types, such as a blend of brown propolis, green propolis, red propolis, or any combination thereof) may comprise a variety of bioactive agents. In some embodiments, a bioactive extract obtained from propolis comprises at least one of the following: fatty and phenolic acids and esters, substituted phenolic esters, flavonoids (e.g., flavones, flavanones, flavonols, dihydroflavonols, chalcones, etc.), mono-, sesqui-, di-, and triterpenes, steroids, aromatic aldehydes and alcohols, naphthalene and stilbene derivatives, caffeoylquinic acid derivatives, lignans, coumarins, prenylated and coumarin derivatives. Bioactive molecules obtained from propolis are known in the art, for example as described by Schindler Machado et al. (2016) *Evid Based Complement Alternat Med.* 2016:6057650, and Trusheva et al. (2006) *Evid Based Complement Alternat Med.* 3(2):249-254, and Huang et al. (2014) *Molecules* 19:19610-19632.

The disclosure is based, in part, on propolis bioactive extracts comprising one or more (e.g., 1, 2, 3, 4, 5, 6, etc.) antioxidants. In some embodiments, the one or more antioxidants, are flavonoids (e.g., isoflavonoids, etc.). In some embodiments, flavonoid bioactives in a propolis bioactive extract promote a sequestration of reactive oxygen species (ROS) generated by DNA damage of the cellular elements subjected to radiation, causing a reduction of oral mucosa extracellular matrix degradation. In some embodiments, flavonoids are present in a propolis bioactive extract in a concentration ranging from about 100 µg/mL to about 500 µg/mL (e.g., about 100 µg/mL, about 150 µg/mL, about 200 µg/mL, about 250 µg/mL, about 300 µg/mL, about 350 µg/mL, about 400 µg/mL, about 450 µg/mL, etc.), as measured gravimetrically. In some embodiments, flavonoids are present in a propolis bioactive extract in a concentration ranging from about 100 µg/mL to about 200 µg/mL, as measured gravimetrically. In some embodiments, flavonoids are present in a propolis bioactive extract in a concentration ranging from about 150 µg/mL to about 300 µg/mL, as measured gravimetrically. In some embodiments, flavonoids are present in a propolis bioactive extract in a concentration ranging from about 250 µg/mL to about 400 µg/mL, as measured gravimetrically.

In some embodiments, a propolis bioactive extract comprises one or more lipids, one or more waxes, or a combination of one or more lipids and one or more waxes. In some embodiments, the total lipid and wax concentration of a propolis bioactive extract ranges from about 25 µg/mL to about 750 µg/mL (e.g., about 25 µg/mL, 50 µg/mL, 75 µg/mL, 100 µg/mL, 150 µg/mL, 200 µg/mL, 300 µg/mL, 350 µg/mL, 500 µg/mL, 650 µg/mL, etc.), as measured gravimetrically. In some embodiments, the total lipid and wax concentration of a propolis bioactive extract ranges from about 25 µg/mL to about 100 µg/mL, as measured gravimetrically. In some embodiments, the total lipid and wax concentration of a propolis bioactive extract ranges from about 75 µg/mL to about 250 µg/mL, as measured gravimetrically. In some embodiments, the total lipid and wax concentration of a propolis bioactive extract ranges from about 300 µg/mL to about 550 µg/mL, as measured gravimetrically.

Marine Algal Bioactive Extracts

In some embodiments, a composition comprises a bioactive extract obtained from a marine algae. In some embodiments, the bioactive extract is a powder produced by drying and grinding up marine algae. Methods of producing marine algal extracts (e.g., powders) are known, for example as described by Costa et al. (2010) *Biomedicine and Pharmacology* 64:21-28.

Marine algae are generally classified in four families: rhodonphyceae (red algae), phaeophyceae (brown algae), cyanophaeceae (blue-green algae), and chlorophyceae (green algae). The identification and classification of marine algae is described, for example by AlgaeBase (Guiry, M. D. & Guiry, G. M. 2018. AlgaeBase. World-wide electronic publication, National University of Ireland, Galway; www.algaebase.org).

In some embodiments, a marine algal bioactive extract comprises one or more types of red algae. Examples of red algae include but are not limited to *Rhodophyta* species (e.g., *Rhodophyta graciliara caudata*, etc.), *Porphyra* species (e.g., *Porphyra haitanensis*, etc.), *Pterocladiella* species (e.g., *Pterocladiella capillacea*, etc.), *Osmundaria* species (e.g., *Osmundaria obtusiloba*, etc.), *Gelidium* species (e.g., *Gelidium cartilagenium*, etc.), *Chondrococcus* species (e.g., *Chondrococcus hornemannii*, etc.), and Hypnea species (e.g., *Hypnea musciformi*, etc.). In some embodiments, a marine algal bioactive extract comprises *Porphyra haitanensis*.

In some embodiments, a marine algal bioactive extract comprises one or more types of brown algae. Examples of brown algae include but are not limited to *Laminaria* species (e.g., *Laminaria japonica*, etc.), *Sargassum* species (e.g., *Sargassum wightii*, *Sargassum filipendula*, etc.), *Spatoglossum* species (e.g., *Spatoglossum schroderi*, etc.), *Padina* species (e.g., *Padina tetrastromatica*, etc.), *Dictyota* species (e.g., *Dictyota cervicornis*, *Dictyota menstrualis*, *Dictyota myrtensii*, etc.), *Dictyopteris* species (e.g., *Dictyopteris delicatula*, etc.). In some embodiments, a marine algal bioactive extract comprises *Laminaria japonica*.

In some embodiments, a marine algal bioactive extract comprises one or more types of green algae. Examples of green algae include but are not limited to Ulva species (e.g., *Ulva latuca*, *Ulva arasakii*, *Ulva armoricana*, *Ulva clathrata*, *Ulva conglobate*, *Ulva fasciata*, *Ulva pertusa*, *Ulva reticulate*, *Ulva rigida*, *Ulva rotundata*, etc.), *Enteromorpha* species (e.g., *Enteromorpha linza*, *Enteromorpha clathrata*, *Enteromorpha compressa*, *Enteromorpha intestinalis*, *Enteromorpha prolifera*, etc.), *Monostroma* species (e.g., *Monostroma latissimum*, *Monostroma nitidum*, *Monostroma angicava*, etc.), *Codium* species (e.g.,), *Caulerpa* species (e.g., *Caulerpa brachyous*, *Caulerpa cupressoides*, *Caulerpa lentillifera*, *Caulerpa prolifera*, *Caulerpa racemosa*, *Caulerpa sertularioides*, etc.), *Bryopsis* species (e.g., *Bryopsis plumose*, etc.), *Halimeda* species (e.g., *Halimeda monde*, etc.), *Capsosiphon* species (e.g., *Capsosiphon fulvescens*, etc.), and *Chaetomorpha* species (e.g., *Chaetomorpha antennenina*, etc). In some embodiments, a marina algal bioactive extract comprises *Ulva latuca*. In some embodiments, a marina algal bioactive extract comprises *Enteromorpha linza*. In some embodiments, a marina algal bioactive extract comprises *Ulva latuca* and *Enteromorpha linza*.

In some embodiments, a marine algal bioactive extract comprises one or more types of blue-green algae. Examples of blue-green algae include but are not limited to *Microcystis* species (e.g., *Microcystis aeruginosa*, etc.), *Nostoc* species (e.g., *Nostoc linckia*, *Nostoc spongiaeform*, etc.), *Lyngbya* species (e.g., *Lyngbya majuscule*, *Lyngbya bouillonii*, *Lyngbya sordida*, etc.), *Symploca* species, *Calothrix* species, etc.

A bioactive extract may comprise a combination of marine algal species, for example at least one green marine algal species (e.g., 2, 3, 4, 5, or more green algae species), at least one red marine algal species (e.g., 2, 3, 4, 5, or more red algae species), and/or at least one brown marine algal species (e.g., 2, 3, 4, 5, or more brown algae species). For example, a marine algal bioactive extract may comprise the following species: *Enteromorpha linza*, *Ulva lactula*, *Porphyra haitanensis*, and *Laminaria japonica*. In some embodiments, a marine algal extract does not comprise (e.g., lacks one or more classes of marine algal species, such as red algae green algae, brown algae, and blue-green algae). In some embodiments, a marine algal extract lacks blue-green algae.

The ratio of each type of marine algal species in a mixture from which a marine algal bioactive extract is produced can vary. For example, in some embodiments, a mixture comprises green and brown marine algae in a ratio ranging from about 5:1 to about 1:5 (e.g., 1:1, 1:2, 1:3, 1:4, 1:5, 2:1, 2:3, 2:4, 2:5, 3:1, 3:2, 3:4, 3:5, 4:1, 4:2, 4:3, 4:5, 5:1, 5:2, 5:3, 5:4, etc.). In some embodiments, a mixture comprises green and red algae in a ratio ranging from about 5:1 to about 1:5 (e.g., 1:1, 1:2, 1:3, 1:4, 1:5, 2:1, 2:3, 2:4, 2:5, 3:1, 3:2, 3:4, 3:5, 4:1, 4:2, 4:3, 4:5, 5:1, 5:2, 5:3, 5:4, etc.). In some embodiments, a mixture comprises brown and red algae in a ratio ranging from about 5:1 to about 1:5 (e.g., 1:1, 1:2, 1:3, 1:4, 1:5, 2:1, 2:3, 2:4, 2:5, 3:1, 3:2, 3:4, 3:5, 4:1, 4:2, 4:3, 4:5, 5:1, 5:2, 5:3, 5:4, etc.). In some embodiments, a propolis mixture comprises green, brown, and red algae in a ratio that ranges from about 5:1:1 to about 1:5:1, to about 1:1:5 (e.g., 1:1:1, 1:2:1, 2:1:1, 1:1:2, etc.).

The amount of a marine algae bioactive extract in a composition of the disclosure may vary. In some embodiments, a composition as described herein (e.g., a drug delivery composition) comprises between about 0.1% w/w and about 20% w/w of marine algal bioactive extract. The amount of marine algal extract may be expressed as a percent weight of each marine algal species extract in the composition, or as the total amount of marine algal bioactive extract in the composition. For example, a composition may comprise 20% w/w of total marine algal bioactive extract, of which four different types of marine algal species extract contribute 5% w/w.

In some embodiments, a composition comprises between about 0.1% w/w and about 5% w/w of a marine algal bioactive extract. In some embodiments, a composition comprises about 1%, about 2%, about 3%, about 4%, or about 5% w/w of marine algal bioactive extract. In some embodiments, a composition comprises between about 3% and about 7% w/w of marine algal bioactive extract. In some embodiments, a composition comprises between about 5% and about 20% w/w of marine algal bioactive extract.

Extracts obtained from marine algae (e.g., one or more marine algal species, such as a blend of two, three, four, or more marine algal species) may comprise a variety of bioactive agents. In some embodiments, a marine algal bioactive extract comprises one or more of the following: sulfated polysaccharides, phorolotannins, xanthins (e.g., fucoxanthin, asthaxanthin, etc.), phloroglucinols, polyphenols, carotenoids, and sesquiterpenes.

The disclosure is based, in part, on marine algal bioactive extracts comprising sulfated polysaccharides (e.g., non-animal sulfated polysaccharides). Sulfated polysaccharides are anionic, carbohydrate polymers that are generally classified based upon the class of marine algae (e.g., brown, green, red) from which they are obtained. Typically, brown marine algae (e.g., phaeophyceae) produce sulfated fucans or fucoidans, which may comprise fucose, xylose, urinuc acid, and/or galactose sugars. Red marine algae (e.g., rhodonphyceae) generally produce galactans and carrageenans, which may comprise sulfated galactose and 3,6-anhydrogalactose sugars. Green marine algae produce ulvans, which include sulfated rhamnose linked to either glucuronic acid, iduronic acid, or xylose. Classification of marine algal sulfated polysaccharides is known, for example as described by Pater (2012) 3 Biotech 2(3):171-185.

Bioactive characteristics of sulfated polysaccharides may vary. In some embodiments, a marine algal bioactive extract comprises one or more sulfated polysaccharides having antioxidant activity. Examples of antioxidant sulfated polysaccharides include but are not limited to ulvans extracted from Codia, Ulva, and Enteromorpha, galactans extracted from *Caulerpa*, fucans and fucodans extracted from *Laminaria japonicum*, and galactans and carrageenans from *Porphyra haitanensis*. In some embodiments, a marine algal bioactive extract comprises one or more sulfated polysaccharides having a bioactivity selected from anticoagulant activity, immunomodulatory activity, antitumor activity, antiviral activity, and antinociceptive activity. Methods of extraction and functional characterization of marine algal sulfated polysaccharides is known, for example as described by Costa et al. (2010 *Biomedicine and Pharmacotherapy* 64:21-28; Zhang et al. (2010) *Carbohydrate Polymers* (2010) 82:118-121; and Wang et al. (2014) *Mar. Drugs* 12:4984-5020, the entire contents of each of which are incorporated herein by reference.

In some embodiments, a marine algal bioactive extract comprises one or more sulfated polysaccharides selected from an ulvan, carrageenan, and fucan, or a combination of the forgoing. In some embodiments, a bioactive extract comprises one or more ulvans, for example ulvans obtained from *Ulva latuca* and/or *Enteromorpha linza*. In some embodiments, a bioactive extract comprises one or more galactans and/or one or more carrageenans, for example galactans and/or carrageenans obtained from *Porphyra haitanensis*. In some embodiments, a bioactive extract comprises one or more fucans and/or fucoidans, for example one or more fucans and/or fucoidans obtained from *Laminaria japonica*.

Bioactive Extracts from Carrot

In some embodiments, the disclosure relates to bioactive extracts comprising combinations of molecules that are useful for promoting tissue regeneration (e.g., a tissue regeneration bioactive extract). In some embodiments, a tissue regeneration bioactive extract comprises one or more bioactive molecules obtained from carrots (e.g., carotenoids, etc.), one or more Vitamin A derivatives, one or more scaffold molecules, or a combination of any of the foregoing.

In some embodiments, the one or more bioactive agents are obtained (e.g., extracted) from carrot (e.g., *Dacus carota*, or a cultivar or variant thereof). Generally, carrots comprise a variety of bioactive molecules, for example, carotenoids and phenolic compounds. Examples of carotenoids extractable from carrots include but are not limited to α-carotene and β-carotene. Examples of phenolic compounds extractable from carrots include chlorogenic acid, hydroxycinnamic acid derivatives, ferulic acid, dicaffeoylquinic acid, and anthocyanins. In some embodiments, one or more bioactive molecules are extracted from a carrot in the form of "carrot oil", which is typically produced by either a solvent-based or pressure-based extraction method, for example cold-pressing lipids and biomolecules from carrot seeds and/or taproot; neutral oil (e.g., mineral oil)-based extraction of compounds from carrot seeds and/or taproot; alcohol-based extraction of biomolecules from carrot seeds and/or taproot; supercritical carbon dioxide extraction methods, etc. Methods of extracting bioactive molecules are also described, for example by U.S. Pat. No. 7,141,083, U.S. Publication No. 2008-0233238, and Japanese Patent No. JPH0676591.

In some embodiments, a tissue regeneration bioactive extract comprises one or more B vitamin complexes (e.g., one or more members of a B vitamin complex). The B vitamin complex generally refers to a complex comprising all essential water soluble vitamins except vitamin C. In some embodiments, B vitamin complex comprises thiamine (vitamin B1), riboflavin (vitamin B2), niacin (vitamin B3), pantothenic acid (vitamin B5), pyridoxine (vitamin B6), biotin, folic acid, and cobalamins (vitamin B12). In some embodiments, a tissue regeneration bioactive extract comprises pantothenic acid or a derivative, analog, or salt thereof. Examples of pantothenic acid derivatives and analogs include pantothenol and dexpanthenol. In some embodiments, one or more B vitamin complexes is a derivative of pantothenic acid or a derivative or analogue thereof. In some embodiments, a B vitamin complex comprises dexpanthenol.

The total amount of bioactive extract derived from carrot in a composition may vary. In some embodiments, the amount of bioactive extract obtained from carrot (e.g., carrot oil extract) ranges from about 1% (w/w) and about 5% (w/w), for example about 1%, about 2%, about 3%, about 4%, or about 5% w/w. In some embodiments, a tissue regeneration bioactive extract does not comprise (e.g., lacks) bioactive extract derived from carrot. In some embodiments, a tissue regeneration bioactive extract further comprises Aloe vera, for example Aloe vera extract.

The disclosure is based, in part, in tissue regeneration bioactive extracts comprising one or more scaffold molecules. As used herein, a "scaffold molecule" is a molecule, such as a protein or a polymer, that provides a substrate to which cells (e.g., stem cells, such as mesenchymal stem cells) may adhere and which promote cell attachment, growth, and differentiation. In some embodiments, the one or more scaffold molecules is a protein (e.g., an animal protein, extracellular matrix (ECM) protein, etc.). In some embodiments, the protein comprises collagen, albumin, or a combination thereof. In some embodiments, the protein comprises one or more serum proteins, for example albumin (e.g., bovine serum albumin), fish serum proteins, pig serum proteins, etc. In some embodiments, a composition comprises 1, 2, 3, 4, 5, 6, 7, 8, 9, 10, or more scaffold molecules.

In some embodiments, a scaffold molecule is a polymer, for example a polysaccharide polymer, for example hyaluronic acid, chitosan, or alginate. In some embodiments, the polysaccharide polymer is hyaluronic acid. Hyaluronic acid is a glycosaminoglycan polymer that comprises repeating subunits of glucuronic acid and N-acetyl-D-glucosamine. Typically, hyaluronic acid is classified according to its molecular weight. Low molecular weight hyaluronic acid (MWHA) generally has a molecular weight less than 100 kDa. Medium MWHA generally has a molecular weight between 100 and 300 kDa. High MWHA generally has a molecular weight above 300 kDa. In some embodiments, the scaffold molecule comprises medium MWHA.

The total amount of scaffold molecules in a composition may vary. In some embodiments, the amount of scaffold molecules ranges from about 0.1% (w/w) and about 10% (w/w), for example about 0.1%, about 0.5%, about 1%, about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, or about 20% w/w.

The ratio of bioactive molecules to scaffold molecules in a tissue regeneration bioactive extract can vary. For example, in some embodiments, a composition comprises bioactive molecules and scaffold molecules in a ratio ranging from about 10:1 to about 1:10 (e.g., 1:1, 1:2, 1:3, 1:4, 1:5, 1:6, 1:7, 1:8, 1:9, 1:10 2:1, 2:3, 2:4, 2:5, 2:6, 2:7, 2:8, 2:9, 3:1, 3:2, 3:4, 3:5, 3:6, 3:7, 3:8, 3:9, 4:1, 4:2, 4:3, 4:5, 4:6, 4:7, 4:8, 4:9, 5:1, 5:2, 5:3, 5:4, 5:6, 5:7, 5:8, 5:9, 6:1, 6:2, 6:3, 6:4, 6:5, 6:7, 6:8, 6:9, 7:1, 7:2, 7:3, 7:4, 7:5, 7:6, 7:8, 7:9, 8:1, 8:2, 8:3, 8:4, 8:5, 8:6, 8:7, 8:9, 9:8, 9:7, 9:6, 9:5, 9:4, 9:3, 9:2, 9:1, 10:1 etc.).

Bioactive Extracts from Lemon Balm

In some aspects, the disclosure relates to bioactive extracts obtained from *Melissa officinalis*, also referred to as Lemon balm. Lemon balm is a plant member of the mint family, Lamiaceae. Lemon balm is native to Europe and central Asia but generally may be cultivated around the world. Cultivars of *M. officinalis* include *M. officinalis citronella, M. officinalis lemonella, M. officinalis* Quedlinburger, *M. officinalis* lime, *M. officinalis variegata, M. officinalis aurea*, and *M. officinalis* Quedlinburger Niederliegende.

Bioactive molecules produced by Lemon balm include but are not limited to polyphenolic compounds, eugenol, tannins, and terpenes (e.g., monoterpenes, tri-terpenes, terpenoids etc.), for example (+)-citronellal, 1-octen-3-ol, 10-α-cadinol, 3-octanol, 3-octanone, α-cubebene, α-humulene, β-bourbonene, caffeic acid, caryophyllene, caryophyllene oxide, catechin, chlorogenic acid, cis-3-hexenol, cis-ocimene, citral A, citral B, copaene, δ-cadinene, eugenyl acetate, γ-cadinene, geranial, geraniol, geranyl acetate, germacrene D, isogeranial, linalool, luteolin-7-glucoside, methylheptenone, neral, nerol, octyl benzoate, oleanolic acid, pomolic acid ((1R)-hydroxyursolic acid), protocatechuic acid, rhamnazin, rosmarinic acid, stachyose, succinic acid, thymol, trans-ocimene, ursolic acid, and harmine.

In some embodiments, bioactive molecules are produced in the leaves and stems of Lemon balm. Typically, bioactive molecules are isolated (e.g., extracted) from Lemon balm leaves in the form of an "essential oil", also referred to as a "volatile oil". Methods of extracting bioactive compounds from Lemon balm are known in the art, for example by aqueous extraction (e.g., as described by Nolkemper et al. (2006) *Planta Med.* 72(15):1378-1382) or by pressure-based extraction (e.g., as described by Dastmalchi et al. (2008) *LWT—Food Science and Technology,* 41 (3):391-400).

In some embodiments, a bioactive extract obtained from *Melissa officinalis* comprises one or more monoterpenes or monoterpenoids, for example citronellal, neral, and/or geranial. In some embodiments, a bioactive extract obtained from *Melissa officinalis* comprises rosmarinic acid. In some embodiments, terpenes and rosmarinic acid present in bioactive extracts of *Melissa officinalis* have antiviral (e.g., antiretroviral, such as anti-Herpes or anti-HIV) activity. Antiviral activity of bioactive extracts obtained from *Melissa officinalis* are described, for example by Allahverdiyev et al. (2004) *Phytomedicine* 11(7-8):657-61, and Geuenich et al. (2008) *Retrovirology* 5:27.

In some embodiments, a composition as described by the disclosure comprises a bioactive extract obtained from *Melissa officinalis* and one or more antiviral agents, for example, acyclovir, valacyclovir, penciclovir, famciclovir, docosanol, avacavir, cidofovir, efavirenz, entecavir, imiquimod, lopinavir, emtricitabine, lamivudine, tenofovir, zidovudine, doravirine, etravine, nevirapine, rilpivirine, atazanavir, darunavir, fosamprenavir, sasquinavir, tipranivir, efuviritide, maraviroc, ralteravir, ibalzumab, cobicistat, or any combination thereof.

In some embodiments, a composition comprising a bioactive extract obtained from *Melissa officinalis* further comprises one or more B vitamin complexes (e.g., one or more members of a B vitamin complex). In some embodiments, the one or more members of the B vitamin complex are cobalamins (e.g., vitamin B12). In some embodiments, the cobalamins are methylated (e.g., methylcobalamins) or cyanated (e.g., cyanocobalamin). In some embodiments, the composition comprises a combination of methylcobalamin and cyanocobalamin. Without wishing to be bound by any particular theory, cobalamins are useful, in some embodiments, for promoting peripheral nerve repair and reducing neuropathic pain.

The amount of a cobalamin (e.g., methylcobalamin and/or cyanocobalamin) in a composition may vary. In some embodiments, the amount of methylcobalamin in a composition ranges from about 0.1% (w/w) and about 0.5% (w/w), for example about 0.1%, about 0.2%, about 0.3%, about 0.4%, or about 0.5% w/w. In some embodiments, the amount of cyanocobalamin in a composition ranges from about 0.1% (w/w) and about 2.% (w/w), for example about 0.1%, about 0.2%, about 0.3%, about 0.4%, about 0.5%, about 0.6%, about 0.7%, about 0.8%, about 0.9%, about 1.0%, about 1.1%, about 1.2%, about 1.3%, about 1.4%, about 1.5%, about 1.6, about 1.7, about 1.8, about 1.9, or about 2.0% w/w.

The ratio of methylcobalamin to cyanocobalamin in a composition can vary. For example, in some embodiments, a composition comprises methylcobalamin to cyanocobalamin in a ratio ranging from about 10:1 to about 1:10 (e.g., 1:1, 1:2, 1:3, 1:4, 1:5, 1:6, 1:7, 1:8, 1:9, 1:10 2:1, 2:3, 2:4, 2:5, 2:6, 2:7, 2:8, 2:9, 3:1, 3:2, 3:4, 3:5, 3:6, 3:7, 3:8, 3:9, 4:1, 4:2, 4:3, 4:5, 4:6, 4:7, 4:8, 4:9, 5:1, 5:2, 5:3, 5:4, 5:6, 5:7, 5:8, 5:9, 6:1, 6:2, 6:3, 6:4, 6:5, 6:7, 6:8, 6:9, 7:1, 7:2, 7:3, 7:4, 7:5, 7:6, 7:8, 7:9, 8:1, 8:2, 8:3, 8:4, 8:5, 8:6, 8:7, 8:9, 9:8, 9:7, 9:6, 9:5, 9:4, 9:3, 9:2, 9:1, 10:1 etc.).

Therapeutic Methods

The disclosure relates, in some aspects, to methods for delivering compositions (e.g., therapeutic compositions) to a cell or a subject. In some embodiments, methods of administering compositions described by the disclosure are useful for the treatment of certain diseases and disorders associated with damaged tissue or compromised skin (e.g., damaged skin or cells), for example mucositis, ulcers, wounds (e.g., surgical incisions, etc.), burns, and tissue damage due to viral infection (e.g., peripheral nerve damage resulting from infection with herpesvirus 1 (HSV-1), or blisters resulting from infection with herpesvirus 2 (HSV-2), varicella infection, etc.).

The terms "treatment," "treat," and "treating" refer to reversing, alleviating, delaying the onset of, or inhibiting the progress of a "pathological condition" (e.g., a disease, disorder, or condition, or one or more signs or symptoms thereof) described herein. In some embodiments, treatment may be administered after one or more signs or symptoms have developed or have been observed. In other embodiments, treatment may be administered in the absence of signs or symptoms of the disease or condition. For example, treatment may be administered to a susceptible individual prior to the onset of symptoms (e.g., in light of a history of symptoms and/or in light of genetic or other susceptibility factors). Treatment may also be continued after symptoms have resolved, for example, to delay or prevent recurrent infections of herpesvirus.

As disclosed herein, compositions may be administered by any suitable route. For example, an effective amount of the composition and/or other therapeutic agents can be administered to a subject by any mode that delivers the agent to the desired tissue, e.g., skin, mucosal tissue, nervous system tissue, muscle tissue, etc. In some embodiments, compositions are administered topically. Other suitable routes of administration include but are not limited to oral, parenteral, intravenous, intraperitoneal, intranasal, intramuscular, sublingual, intratracheal, inhalation, subcutaneous, ocular, vaginal, and rectal. Systemic routes include oral and parenteral.

For oral administration, compositions can be administered in the form of tablets, pills, dragees, capsules, liquids, mouthwashes, gels, syrups, slurries, suspensions and the like. In some embodiments, the disclosure provides compositions in the form of a medicated mouthwash, spray, gel, cream, ointment, or dentifrice, which in some embodiments, eliminates the bacterial biofilm responsible for infections and periodontal diseases, and promotes wound healing action of the oral mucosa providing a faster recovery of the injured tissue. In some embodiments, compositions for oral delivery comprise a combination of propolis bioactive extract and one or more surfactants (e.g., one or more biosurfactants).

In some embodiments, a composition formulated for oral delivery is compatible with the use of autologous grafting techniques, for example biomaterials such as platelet-rich fibrin (PRF). In some embodiments, compositions of the disclosure do not chemically interact with grafted tissue and associated clots, making the compositions suitable for use by subject having undergone dental procedures (e.g., dental tissue grafting, etc.).

Accordingly, in some embodiments, compositions described herein are useful for treating of mucositis (e.g., oral lesions caused by radiotherapy, etc.). Mucositis is an inflammation and ulceration of mucous tissue in the oral cavity, which typically is caused by cancer chemotherapy and/or radiotherapy.

In some embodiments, the disclosure provides a method for treating oral cavity lesions in a subject (e.g., a subject having mucositis), the method comprising administering an composition (e.g., an oral composition) as described by the disclosure to a subject having one or more oral cavity lesions. In some embodiments, the oral composition comprises a bioactive extract obtained from propolis. In some embodiments, the oral composition is administered in the form of a mouthwash or an aqueous oral solution.

In some embodiments, a subject having or suspected of having mucositis has been subjected to chemotherapy (e.g., administration of one or more doses of a chemotherapeutic agent) and/or radiotherapy (e.g., administration of one or more doses of therapeutic radiation, for example head and neck radiotherapy). In some embodiments, a subject has been previously administered a chemotherapy, radiotherapy, or a combination of chemotherapy and radiotherapy. In some embodiments, a subject having or suspected of having mucositis has been subjected to total-body irradiation in advance of receiving a hematopoietic stem cell transfer.

In some embodiments, compositions (e.g., oral compositions) described by the disclosure are useful for treating tissue that has been mechanically compromised. In some embodiments, a subject having mechanically compromised oral tissue has undergone buco-maxillofacial surgery, for example a dental implant procedure. In some embodiments, an oral composition comprising a bioactive extract obtained from propolis is compatible with biomaterials commonly used in oral surgery (e.g., platelet-rich fibrin, etc.) and reduces the chances, relative to the use of alcohol-based compositions such as antiseptic mouthwashes, that a dental implant will be rejected by a subject's immune system.

In some embodiments, administration of an oral composition as described herein inhibits bacterial biofilm formation and/or growth in a subject (e.g., biofilm formation on mucosal tissue and/or in the oral cavity of a subject). The elimination of the bacterial biofilm of the ulcerated mucosa results, in some embodiments, in the decreased of the polymorphonuclear cells infiltrate and subsequently reduction of the release of pro-inflammatory mediators such as TNF-α, IL-1β, IL-6, and major prostaglandins that mediate hyperalgesic pain.

In some aspects, the disclosure relates to methods for topically administering compositions described herein. Pharmaceutical formulations for topical administration include transdermal patches, ointments, lotions, creams, gels, drops, sprays, suppositories, liquids and powders. In addition, conventional pharmaceutical carriers, aqueous, powder or oily bases, or thickeners may be used in pharmaceutical preparations for topical administration. Compositions of the disclosure that are formulated for topical administration are useful, in some embodiments, for treating compromised tissue such as skin. In some embodiments, the formulation is a hydrogel. Generally, a "hydrogel" refers to a network of polymer chains that are hydrophilic and form a colloidal gel in which water is the dispersion medium. In some embodiments, a hydrogel comprises at least 10% w/w water (e.g., about 10%, 20%, 30%, 40%, 50%, 60%, 70%, 80%, 90%, 95%, or 99% water).

"Compromised tissue" (e.g., compromised skin) refers to tissue that has been chemically or mechanically damaged. Examples of compromised tissue include wounds (e.g., cuts, scrapes, puncture wounds, surgical incisions, neuropathic (diabetic) wounds, etc.), burns (e.g., chemical burns, sunburns, heat exposure burns, etc.), blisters, ulcers, muscle and tendon tears, and degenerated nerve tissue.

In some aspects, the disclosure provides a method for treating compromised tissue in a subject, the method comprising topically administering a composition as described herein to a subject in need thereof. In some embodiments, the subject has an ulcer (e.g., a diabetic ulcer). In some embodiments, the subject has a burn, for example a chemical burn (e.g., as a result of a dermatological or cosmetic procedure, such as a chemical skin peel).

In some embodiments, a composition is topically administered to the subject in the form of a spray, foam, gel, or aqueous solution. In some embodiments, a composition is administered to the subject as part of a device or apparatus (e.g., a medical device), for example a solid substrate impregnated with the composition or coated with the composition. Examples of solid substrates that may be impregnated or coated with the composition include but are not limited to fibers (e.g., natural cotton fibers, synthetic fibers such as nylon, etc.), bandages, pads, coverings (e.g., face masks), plastics, metals (e.g., stainless steel, titanium, etc), and the like.

In other embodiments, a composition as described by the disclosure is administered multiple times. In some instances the composition may be administered daily, bi-weekly, weekly, every two weeks, every three weeks, monthly, every two months, every three months, every four months, every five months, every six months or less frequently than every six months. In some instances, the composition is administered multiple times per day, week, month and/or year. For example, the composition can be administered approximately every hour, 2 hours, 3 hours, 4 hours, 5 hours, 6 hours, 7 hours, 8 hours, 9 hours 10 hours, 12 hours or more than twelve hours. In some embodiments, the composition is administered 1, 2, 3, 4, 5, 6, 7, 8, 9, 10 or more than 10 times per day.

Dosage regimens may be adjusted to provide the optimum therapeutic response. For example, the oligonucleotide may be repeatedly administered, e.g., several doses may be administered daily or the dose may be proportionally reduced as indicated by the exigencies of the therapeutic situation. One of ordinary skill in the art will readily be able to determine appropriate doses and schedules of administration of the subject compositions, whether the compositions are to be administered to cells or to subjects.

Aspects of the disclosure relate to methods for use with a subject (e.g., a mammal). In some embodiments, a mammalian subject is human or a non-human primate. Non-limiting examples of non-human primate subjects include macaques (e.g., cynomolgus or rhesus macaques), marmosets, tamarins, spider monkeys, owl monkeys, vervet monkeys, squirrel monkeys, baboons, gorillas, chimpanzees, and orangutans. In some embodiments, the subject is a human subject. Other examples of subjects include domesticated animals such as dogs and cats; livestock such as horses, cattle, pigs, sheep, goats, and chickens; and other animals such as mice, rats, guinea pigs, and hamsters.

EXAMPLES

Example 1: Drug Delivery Compositions

This example describes several embodiments of drug delivery compositions of the disclosure. Generally, drug delivery compositions described here comprise the following components: a carbonate buffer solution, at least two different biosurfactants, at least one hygroscopic agent, at least one antioxidant, and at least one bioactive agent.

The carbonate buffer system has a pH between 7.5 to about 9.5, preferably between 8.0 and 9.0. When administered to compromised tissue of a subject, drug delivery compositions described by the disclosure provide a microenvironment that promotes tissue healing and regeneration. Certain ions present in the buffers increase the concentration of large Na or $NH_4^+$ ions in a composition or in a microenvironment created when the composition is contacted to compromised tissue. The large ions bind to certain molecules on the surface of mammalian cells, such as heparin sulfate (HS), and prevent entry of pathogens into the cells by disrupting binding of microbes, such as bacteria and viruses, to the HS on the surface of target cells. The ability of the compositions described by the disclosure to provide such an environment at this pH is surprising in view of currently available wound healing compositions, which typically have pH values in a neutral to acidic range.

The combination of two biosurfactants in the compositions described herein serves several purposes. In some embodiments, the biosurfactants disrupt the surface tension of cells, such as bacterial cells and cells of compromised tissue, thereby promoting molecular debridement. Additionally, the surfactants assist the bioactive molecules of the composition in penetrating deep into compromised tissue.

The hygroscopic agent provides moisture in the wound bed and promotes adequate hydration of the tissue as it heals. Hygroscopic agents also provide, in some embodiments, a matrix that may serve as a scaffold for cell adhesion and differentiation in tissue regeneration. Antioxidants present in the compositions scavenge free radicals and reduce reactive oxygen species (ROS), which is important for reducing inflammation in the compromised tissue as the healing process occurs. Antioxidants may also function as a preservative in the compositions.

The compositions also include one or more bioactive agents, which are delivered by the composition. As described in the Examples below, the bioactive agent may be substituted or altered to include bioactive molecules that achieve the desired therapeutic outcome. One embodiment of a drug delivery composition formulation described by the disclosure is provided in Table 1 below.

TABLE 1

| CLASS OF INGREDIENT | Min (% w/w) | Max (% w/w) |
|---|---|---|
| Purified Water | 10 | 99.0 |
| Bioactive 1 | 0.10 | 20.00 |
| Bioactive 2 | 0.10 | 10.00 |
| Bioactive 3 | 0.30 | 10.00 |
| Non-ionic Surfactant 1 | 0.10 | 20.00 |

TABLE 1-continued

| CLASS OF INGREDIENT | Min (% w/w) | Max (% w/w) |
| --- | --- | --- |
| Biosurfactant 1 | 0.01 | 6.50 |
| Biosurfactant 2 | 0.01 | 6.50 |
| Non-ionic Surfactant 2 | 0.42 | 15.00 |
| Non-ionic Surfactant 3 | 0.20 | 10.00 |
| Hygroscopic Glycol Polymer | 1.00 | 20.00 |
| Hydrophilic Cellulose Polymer | 0.15 | 10.00 |
| Glycosaminoglycan | 0.01 | 10.00 |
| Lipophilic Antioxidant | 0.01 | 2.92 |
| Carbonate | 0.01 | 5.00 |
| Preservative 1 | 0.01 | 4.50 |
| Preservative 2 | 0.01 | 4.50 |

In summary, the drug delivery compositions described by the specification provide a microenvironment that promotes tissue healing and regeneration by simultaneously providing 1) molecular debridement, 2) adequate hydration, and 3) and anti-inflammatory and antimicrobial activity, such as removal of bacterial biofilm as a result of disruption of scaffold mucopolysaccharide structure or inhibition of pathogen binding to target cells of a subject).

Example 2: Tissue Repair Composition

Reduction of symptoms and complications of RIOM, for example by nutritional support, pain control, prophylaxis, and/or treatment of secondary infections, are currently considered the main cornerstone in the management of RIOM.

Regenerative therapy in dentistry involves the replacement and/or regeneration of oral tissues altered as a result of disease or injury. One of the reported aspects complicating this endeavor has been the complex nature of the tissues found in the oral cavity. These include both mineralized tissues such as the cementum, alveolar bone, and dentin, as well as soft tissues connected by ligaments (periodontal ligament), each comprising distinct cell populations from various tissue origins (ectodermal and mesodermal).

Platelet-Rich Fibrin (PRF) is obtained simply by centrifugation of patient's peripheral blood without anticoagulants and is therefore strictly autologous. This fibrin matrix contains platelets and leukocytes as well as a variety of growth factors and cytokines including transforming growth factor-beta1 (TGF-β1), platelet-derived growth factor (PDGF), vascular endothelial growth factor (VEGF), interleukin (IL)-1β, IL-4, and IL-6. Furthermore, fibrin that forms during the final stages of the coagulation cascade, combined with cytokines secreted by platelets, makes PRF a highly biocompatible matrix especially in damaged sites where the fibrin network acts also as a reservoir of tissue growth factors. Several Control Randomized Trials (RCT) have demonstrated that an autologous PRF is more effective for regeneration of oral tissues rather than any biomaterial available in the market. However, traditional mouthwashes are designed to disinfect the oral cavity, aid the removal of bacterial plaques and prevent caries formation, and are characterized by high concentrations of active compounds of denaturants and antimicrobials. The use of mouthwashes containing ethanol, triclosan and chlorhexidine are not recommended for the rinse of postoperative grafting using PRF because they may dissolve the clot and disintegrate the fibrin membrane, affecting the healing process.

This example describes a tissue repair solution useful for prevention and healing the ulcerative phase of RIOM and as an adjuvant in dental implant surgery. Typically, the mouthwash is applied as a spray solution directly into the lesions of the oral cavity before and after meals, 3 times a day. An example of a tissue repair solution is described in Table 2 below.

TABLE 2

| INGREDIENTS Formula 1 | CLASS OF INGREDIENT | Min (% w/w) | Max (% w/w) |
| --- | --- | --- | --- |
| Propolis (Green) | Bioactive | 0.15 | 5.20 |
| Propolis (Brown) | Bioactive | 0.30 | 7.70 |
| Butylated Hydroxytoluene (BHT) | Lipophilic Antioxidant | 0.01 | 2.92 |
| Propylene Glycol | Hygroscopic Glycol Polymer | 1.00 | 15.00 |
| Polyoxyethylene lauryl ether | Non-ionic Surfactant | 0.18 | 7.00 |
| Polaxamer | Non-ionic Surfactant | 0.20 | 4.00 |
| Rhamnolipid | Biosurfactant | 0.01 | 6.24 |
| Sophorolipid | Biosurfactant | 0.01 | 6.24 |
| Alfa-tocopherol | Antioxidant | 0.00 | 2.00 |
| Potassium Sorbate | Preservative | 0.01 | 5.00 |
| Sorbitol | Sweetener | 0.10 | 5.00 |
| Sodium bicarbonate | Carbonate | 0.50 | 10.00 |
| Purified water | Solvent | 10.00 | 99.00 |

The composition comprises the a drug delivery composition as described in Example 1 and includes bioactives from a balanced blend of high quality propolis extract. In some embodiments, the composition promotes simultaneous biological actions important for tissue repair of the mucosa, such as anti-inflammatory, anti-oxidant, immunological induction, anti-microbial and antifungal actions. The composition is entirely compatible with the use of autologous grafting techniques, as is the case with PRF, since it does not chemically attack the clot and the grafted tissue.

The propolis bioactive complex comprises several groups of flavonoids, isoflavonoids, chalcones and pterocarpans, which possess an anti-bacterial, anti-fungal, and anti-oxidant actions important for the wound healing and for the removal of the bacterial biofilm from the lesion bed in the mucosa and submucosa layers. The high antioxidant action of the isoflavonoid bioactives also promotes a sequestration of reactive oxygen species (ROS) generated by DNA damage of the cellular elements subjected to radiation, causing in its turn the reduction of the oral mucosa extracellular matrix degradation.

The elimination of the bacterial biofilm of the ulcerated mucosa, in some embodiments, results in the decreased of the polymorphonuclear cells infiltrate and subsequently reduction of the release of pro-inflammatory mediators such as TNF-α, IL-10, IL-6, and major prostaglandins that mediates hyperalgesic pain.

The presence of highly tensile biomolecules such as the rhamnolipids and sophorolipid biosurfactants of the drug delivery system promote a biochemical micro-debridation that causes an effective disruption in the polysaccharide matrix of the bacterial biofilm and the removal of devitalized and necrotic tissues caused by the cellular damage.

All these synergistic actions together promote a rapid and effective tissue repair of the injured mucosa.

Example 3: Wound Healing Composition

Chronic wounds fail to progress through the normal pattern of wound repair, but instead remain in a state of chronic inflammation predominantly characterized by abundant peripheral mononuclear (PMN) and macrophage (MF) cellular infiltration. Persisting inflammatory cells play a major role in the generation of pro-inflammatory cytokines (e.g., IL-1, TNF-α, IL-6) and a protease rich and pro-oxidant hostile microenvironment. Increased proteolytic activity (e.g., neutrophil elastase, MMP-8, and gelatinase) leads to degradation of growth factors and structural proteins of the extracellular matrix crucial for repair. Increased ROS ($H_2O_2$, $O_2^-$) can lead to direct damage of cells or extracellular matrix molecules, or contribute to increased expression of matrix metalloproteases (MMPs), such as (MMP-1, -2, -3, -9, and 13). Bacterial biofilms impact chronic non-healing wounds as follows: 1) wounds that contain biofilms may not be identified; 2) ineffective biofilm treatment may delay healing; 3) debridement is one of the most important treatment strategies against biofilms, but does not remove all biofilm, and therefore cannot be used alone; 4) biofilms can reform rapidly; repeated debridement alone is unlikely to prevent biofilm regrowth; however, effective topical antiseptic application within this time-dependent window can suppress biofilm reformation; and 5) biofilms are present in most chronic wounds and are likely to be located both on the surface and in deeper wound layers. Biofilm components (e.g., extracellular adherence protein (Eap), formyl methionyl peptides, N-acetylmuramyl-L-alanyl-D-isoglutamine) may contribute to impaired repair mechanisms of the host by interference with cell-matrix interactions or promoting the inflammatory response.

The following examples describes pharmaceutical delivery compositions in the form of a cellular activating fluidic foam, which includes a bioactive extract comprising sulfated polysaccharides from marine algae, with emollient and healing action, to promote the growth of the granulation tissue, and a hydrogel which includes bacterial biofilm inhibitors such as propolis, baicalin and adrographolide to promote debridement and removal of dead tissues and debris, and to maintain a moist environment conducive to wound healing. One embodiment of the cellular activating fluidic foam is described in Table 3A, and one embodiment of bacterial biofilm mitigation hydrogel is described in Table 3B below.

TABLE 3A

| INGREDIENTS | CLASS OF INGREDIENT | Min (% w/w) | Max (% w/w) |
|---|---|---|---|
| *Enteromorpha linza* extract | Marine algae powder | 0.10 | 5.00 |
| *Ulva lactuca* extract | Marine algae powder | 0.10 | 5.00 |
| *Porphyra haitanensis* extract | Marine algae powder | 0.10 | 5.00 |
| *Laminaria japonica* extract | Marine algae powder | 0.10 | 5.00 |
| *Aloe vera* | Herbal concentrate | 1.00 | 10.00 |
| Butylated Hydroxytoluene (BHT) | Lipophilic Antioxidant | 0.01 | 2.00 |
| Polyethylene Glycol | Hygroscopic Glycol Polymer | 0.10 | 8.00 |
| Propylene Glycol | Hygroscopic Glycol Polymer | 1.00 | 7.00 |
| Brij 35 (Polyoxyethyleneglycol Dodecyl Ether) | Non-ionic Surfactant | 0.10 | 5.00 |
| Cocamidopropyl betaine | Zwitterion surfactant | 0.10 | 5.00 |
| Decyl glucoside | Non-ionic Surfactant | 0.50 | 4.00 |
| Rhamnolipid | Biosurfactant | 0.01 | 8.00 |
| Sophorolipid | Biosurfactant | 0.01 | 8.00 |
| Sodium bicarbonate | Carbonate | 0.10 | 10.00 |
| Purified Water | Solvent | 10.00 | 99.00 |

TABLE 3B

| INGREDIENTS | CLASS OF INGREDIENT | Min (% w/w) | Max (% w/w) |
|---|---|---|---|
| Propolis | Anti-biofilm bioactive | 0.10 | 20.00 |
| Baicalin | Anti-biofilm bioactive | 0.10 | 10.00 |
| Andrographolide | Anti-biofilm bioactive | 0.30 | 10.00 |
| Polaxamer | Non-ionic Surfactant | 0.10 | 20.00 |
| Butylated Hydroxytoulene (BHT) | Lipophilic Antioxidant | 0.01 | 2.92 |
| Rhamnolipid | Biosurfactant | 0.01 | 6.50 |
| Sophorolipid | Biosurfactant | 0.01 | 6.50 |
| Sodium bicarbonate | Carbonate | 0.01 | 5.00 |
| Decyl glucoside | Non-ionic Surfactant | 0.42 | 15.00 |
| PEG | Hygroscopic Glycol Polymer | 1.0 | 20.00 |
| Polyoxyethylene lauryl ether | Non-ionic Surfactant | 0.20 | 10.00 |
| Purified Water | Solvent | 10.00 | 99.00 |

The bioactive components present in the composition act synergistically at various points in the chronic wound healing process. For example, saponosidic compounds present in the Aloe vera phytocomplex, combined with bacterial lipid surfactants, facilitate the removal of bacterial biofilms by disruption of its mucopolysaccharide matrix, thus reducing infection and the inflammatory response in the wound bed.

Marine algal sulfated polysaccharides present in the cellular activating fluidic foam are important anti-oxidants and free radical scavengers, such as hydroxy and superoxide ($H_2O_2$, $O_2$), which reduce pro-oxidant and proteolytic activity preventing the destruction of immune cells, growth factors and the extracellular matrix. Moreover, they can stimulate de immune system by controlling macrophage activity. Sulfated polysaccharides such as carrageenan, ulvan and fucoidan can modify the activity of macrophages increasing bacterial binding and killing activities in colonized wound. The anticoagulant and antithrombotic activity of sulfated polysaccharides also contributes to this synergistic action of the product, preventing the formation of microthrombosis and consequently promoting angiogenesis in the new growing tissue.

Example 4: Cosmetic Skin Repair Composition

This example describes a therapeutic facial skin repair mask impregnated with a composition useful as a cosmeceutical in post-skin peeling-procedures, for example pulsed light, chemical and fractioned laser peeling. The composition may also be used as a regenerative treatment after minor dermatological procedures to remove signs, spots, cysts and freckles.

The composition comprises a biodegradable natural fiber face mask that is impregnated or coated with a drug delivery composition comprising bioactives such as beta-carotene (e.g., derived from carrot oil), alpha-tocopherol, and other important components in the process of dermal regeneration. The bioactives are incorporated into a fluid matrix of hyaluronic acid-dexpanthenol, which play a key role in the preservation of the remaining vegetative tissues after a laser burn, for instance.

Hyaluronic acid (HA) also functions in epidermis is to maintain the extracellular space and providing an open, as well as hydrated, structure for the passage of nutrients. Bioactives and nutrients such as retinoic acid (Vitamin A), alpha-tocopherol (Vitamin E), and Vitamin B5 (dexpanthenol) can be extensively transported through the HA matrix to the tissue under repair. Furthermore, HA is likely to play a multifaceted role in mediation of cellular and matrix events followed by trauma, inflammation, granulation tissue formation, reepithelization and remodeling. One example of the drug delivery composition described in this example is provided in Table 4 below.

TABLE 4

| INGREDIENTS | CLASS OF INGREDIENT | Min (% w/w) | Max (% w/w) |
|---|---|---|---|
| Carrot oil | Bioactive Extract | 0.00 | 5.00 |
| Dexpanthenol | Alcohol derivative of pantothenic acid | 0.30 | 7.70 |
| Alpha-tocopherol | Antioxidant | 0.01 | 2.00 |
| Hyaluronic Acid | Glycosaminoglycan | 0.10 | 10.00 |
| Glycerol | Humectant | 0.50 | 8.00 |
| Butylated Hydroxytoluene (BHT) | Lipophilic Antioxidant | 0.01 | 3.00 |
| PEG | Hygroscopic Glycol Polymer | 0.50 | 10.00 |
| Cocamidopropyl betaine | Zwitterion surfactant | 0.15 | 7.00 |
| Rhamnolipid | Biosurfactant | 0.01 | 8.00 |
| Sophorolipid | Biosurfactant | 0.01 | 8.00 |
| Sodium bicarbonate | Carbonate | 0.50 | 10.00 |
| Fish Non-Hydrolyzed Cartilage Collagen | Animal Protein | 0.01 | 5.00 |
| Pig Skin Hydrolyzed Collagen | Animal Protein | 0.01 | 5.00 |
| Swine Serum Albumin | Animal Plasma Protein | 0.01 | 10.00 |

Example 5: Therapeutic Composition for Herpes Infection

The virus HSV-1 resides in the skin of the lips causing herpes simplex labialis (HSL). Herpes simplex labialis (HSL), also known as cold sores or fever blister, affect millions of Americans. It has been estimated that there are 98 million cases of HSL each year in the US alone.

The initial infection with the virus is by direct contact between the mucous membranes or abraded skin of the lips or mouth and the saliva or other secretions of a person with active primary or recurrent infection. Primary infection with HSV typically occurs in early childhood, often with no symptoms, but may also present as herpetic gingivostomatitis, which is characterized by oral and perioral vesicles (tiny blisters) and ulcers. HSL is preceded by warning signs, which are known as 'prodromal symptoms'; these are feelings of pain, burning, itching, or tingling at the site of subsequent vesicle development. Headache may also occur in the prodromal stage. Within 24 hours of the prodrome, multiple grouped vesicles appear and then weep until they finally form crusts. Such crusts can often bleed quite easily, forming unsightly blackish crusts due to dried blood, which can bleed again when the skin is stretched, e.g., when eating and smiling. These usually heal without scarring within 5 to 15 days. Herpes simplex labialis may cause pain, discomfort, inconvenience, and some amount of psychological and social distress as a result of cosmetic disfigurement.

Following the primary infection, the virus resides in the sensory ganglia (nerve endings) in a latent form. After reactivation, HSV migrates from these sensory ganglia to the outer layer of the skin of the lips or mouth to cause recurrent HSL. The virus replicates in the neurons, leading to recurrent outbreaks. The outbreaks are often induced by exposure to ultraviolet light (sunlight and/or tanning beds), stress, immunosuppression, the common cold, fatigue, fever (hence the term "cold sore" or "fever blister"), overexposure to the wind, extremes in temperature, menstrual periods, pregnancy, dental work, or lip trauma. Perioral laser resurfacing or injection of perioral botulinum toxin or fillers can stimulate an outbreak. At present, there is no cure for HSL, so theoretically, once contracted, the infection remains for life.

This example describes a medicated solution containing natural antiviral bioactive extracts combined with peripheral nerve repair factors for treating herpes simplex labialis (HSL) and genital herpes. The composition comprises a topical formulation for the treatment of cold sore and genital herpes. No topical product currently available on the market addresses both reduction of viral infection and recovery of injured nerve tissue. One embodiment of the topical composition is described in Table 5 below.

TABLE 5

| INGREDIENTS | CLASS OF INGREDIENT | Min (% w/w) | Max (% w/w) |
|---|---|---|---|
| *Melissa officinalis* | Bioactive extract | 0.10 | 5.00 |
| Methylcobalamin | Vitamer of B Complex | 0.01 | 0.50 |
| Cyanocobalamin | Vitamer of B Complex | 0.01 | 2.00 |
| Dexpanthenol | Pro-Vitamin B5 | 0.1 | 5.00 |
| PEG 400 | Hygroscopic Glycol Polymer | 1.00 | 7.50 |
| Hyaluronic Acid | Hydropolymers | 0.01 | 1.50 |
| Hydroxy ethylcelullose | Hydrophilic Cellulose Polymer | 0.10 | 4.00 |
| Ammonium Lauryl Ether Sulfate | Anionic Surfactant | 0.05 | 3.00 |
| Polaxamer | Non-ionic Surfactant | 0.50 | 4.00 |
| Rhamnolipid | Biosurfactant | 0.01 | 6.24 |
| Sophorolipid | Biosurfactant | 0.01 | 6.24 |
| Alfa-tocopherol | Natural Antioxidant | 0.00 | 2.00 |
| Sodium bicarbonate | Carbonate | 0.50 | 10.00 |
| Butylated Hydroxytoluene (BHT) | Lipophilic Antioxidant | 0.01 | 2.92 |

The bioactive extract of *Melissa officinalis* comprises monoterpenoid compounds, such as geranial, α-bisabolol, β-caryophyllene, linalool, neral, citronellal, α-cadinol, β-cadinene, and others, that have synergistic antiviral action against HSV-1 and HSV-2. In addition to monoterpenoid bioactives, bioactive extracts of *Melissa officinalis* comprise polyphenolic compounds, such as rosmarinic acid that exhibit antiviral activity for both herpes labialis (HSV-1) and genital herpes (HSV-2). In some embodiments, the composition further comprises (or is co-administered with) one or more antiviral agents (e.g., acyclovir, etc.) that is currently used to treat HSV infection.

Methylated vitamin B12 and methylcobalamin, have been observed to be involved with the mechanism of repair of degenerate and injured peripheral nerves, as well as reducing neuropathic pain and promoting neural growth.

The biosurfactants and ions present (via the buffering system) in the composition may, in some embodiments, block virus entry into target cells by interfering with binding of HS on the cellular surface.

Example 6: Assessment of Tissue Repair Hydrogel Formulations in an Ex Vivo Porcine Dermal Model with Biofilm Formation This example describes experiments to investigate efficacy of four different wound treatments (Formulations A, B, C, and D) in a porcine dermal explant model. Briefly, 3-day old mature explants were treated with the gel formulations for 24 h or 72 h followed by recovery of the microbial survivors. Three representative microbial species were used in this study: methicillin-resistant *Staphylococcus aureus* (Gram positive), *Pseudomonas aeruginosa* (Gram negative), and *Candida albicans* (yeast).

Overall, the tissue healing formulations tested performed well at the 72 h treatment time, showing remarkably higher level of efficacy of the treatments relative to the 24 h time, with ≤1.5 log of the microbial load across all species evaluated. Important to note here is that the treatments were not reapplied, rather the original treatment was left on the explants for the 72 h treatment time.

Materials and Methods

Test formulations: Five different tissue healing formulations containing propolis (Formulations A, B, C, and D) were tested. Each formulation was a hydrogel containing a different concentration of active agent (e.g., propolis). One hydrogel without active agent was tested as a negative control (excipient). For each hydrogel formulation, approximately 2 mL was applied to each explant is used in the study.

Test organisms: Efficacy against Gram-positive and Gram-negative bacteria, as well as fungal species, was tested. Species and associated ATCC numbers are listed in Table 6.

TABLE 6

| Target category | Species | ATCC Number |
| --- | --- | --- |
| Gram-positive | *Staphylococcus aureus* | USA300 (MRSA) |
| Gram-negative | *Pseudomonas aeruginosa* | BAA-47 |
| Yeast | *Candida albicans* | 10231 |

Biofilm Establishment

Porcine tissue for explants was obtained from a USDA-licensed facility that uses precision leveling technology to prepare the porcine dermis with a specific thickness of approximately 2 mm. Using a punch biopsy, the tissue was cut into circular explants that are approximately 12 mm in diameter and artificially wounded using a Dremel tool to create a wound roughly 2 mm in diameter with a 1.5 mm deep cavity. The explants were then extensively washed and sterilized using chlorine gas. Prior to inoculation and application of the test formulations, explants were placed on 0.5% agar in an incubator at 37° C. for approximately 2 h to equilibrate. The explants were then inoculated with 15-20 μL of log phase cultures of the specified bacteria, or 48 h culture of *C. albicans*, at approximately $10^5$ CFU per explant, and allowed to incubate for 3 days on 0.5% agar with daily transfer to fresh agar plates.

Treatment

The 3-day old explants were washed for 2 min in 2 mL of sterile PBS followed by treatment with the test compositions. Formulations A, B, C, and D were loaded into 10 mL syringes to allow for controlled dosing of the explants with approximately 2 mL of the formulations. After the wash, explants were transferred to the individual wells of a 24-well plate, followed by the addition of the test formulations. The plates were then placed in the incubator for 24 h. In the second round of screening, the treatment time was extended to 72 h to evaluate whether there was benefit to extending the treatment time. All of the four formulations and vehicle control were treated the same. After the designated treatment time, surviving bioburden was recovered from all of the explants and enumerated via serial dilution and plating.

Recovery of Surviving Bacteria

After the 24 h or 72 h incubation, the surviving bacteria and yeasts were recovered from the tissue and enumerated. First, the remaining formulations were gently removed from the explants by tipping the explants followed by two washes in 2 mL of sterile PBS (2 min each time) to remove any remaining materials. The washed explants were then placed in a 15 mL centrifuge tube containing 2 mL of Dey/Engley broth, a general neutralizer. The explants were vortexed for 10 s and subjected to a series of 5 sonication debridement steps: 90 s sonication/60 s rest intervals. The samples were vortexed again to ensure homogeneity, serially diluted, and spot plated (10 μL sample/spot, triplicate) up to dilution −6 and spread plated where necessary (200 μL of undiluted recovery solution).

Efficacy Data

Figure 2:
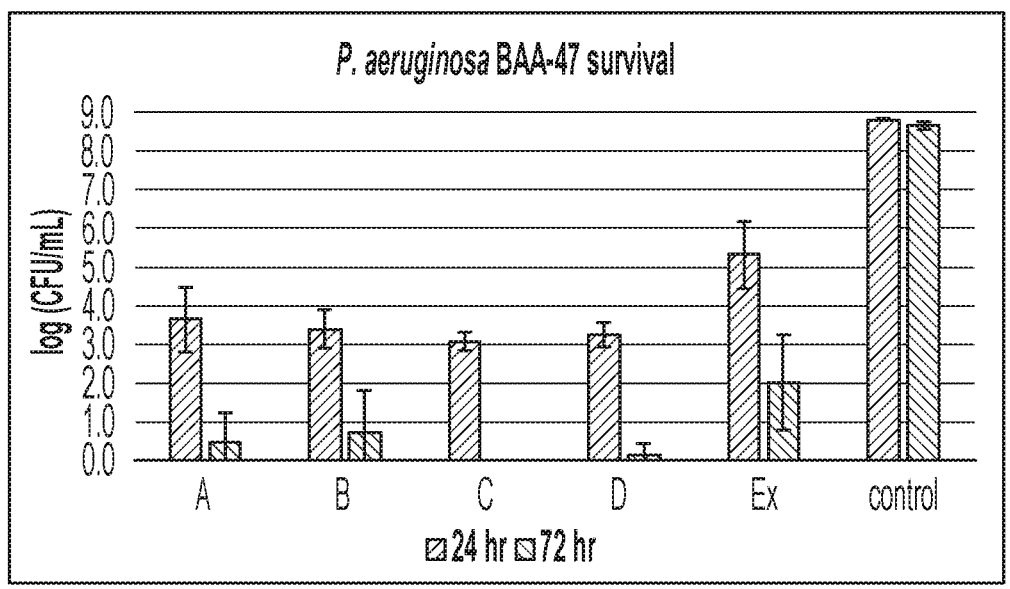
FIG. 2 shows representative data for efficacy of tissue repair formulations against 3-day-old *P. aeruginosa* biofilms. Both daily and single applications were evaluated. Note that the data are presented as microbial survivors. Ex=excipient.
Figure 3:
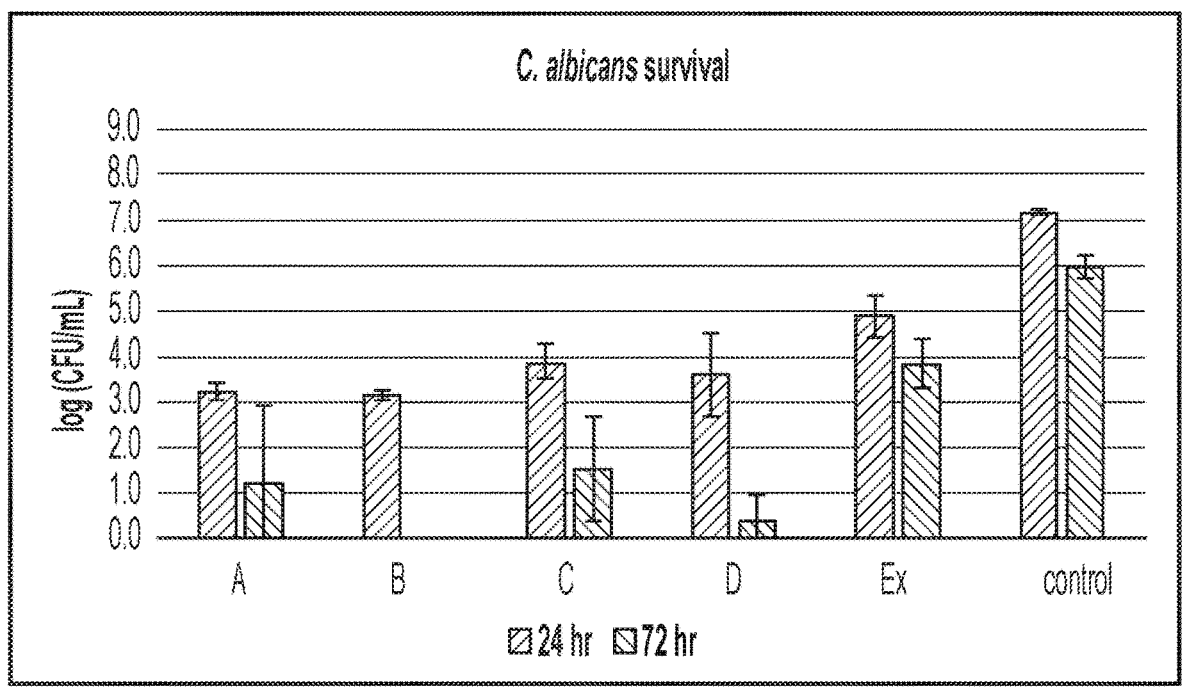
FIG. 3 shows representative data for efficacy of tissue repair formulations against 3-day-old *C. albicans* biofilms. Both daily and single applications were evaluated. Note that the data are presented as microbial survivors. Ex=excipient.

Data are summarized in Table 7 and FIGS. 1-3.

TABLE 7

| | Treatment group | | | | | |
| --- | --- | --- | --- | --- | --- | --- |
| | *S. aureus* USA 300 | | *P. aeruginosa* BAA-47 | | *C. albicans* 10231 | |
| | Treatment time | | | | | |
| | 24 h | 72 h | 24 h | 72 h | 24 h | 72 h |
| Formulation A | 4.87 ± 0.69 | 0.66 ± 0.68 | 3.65 ± 0.84 | 0.48 ± 0.75 | 3.24 ± 0.18 | 1.20 ± 1.72 |
| Formulation B | 5.08 ± 0.43 | 0.17 ± 0.35 | 3.40 ± 0.50 | 0.72 ± 1.08 | 3.17 ± 0.11 | 0.00 ± 0.00 |
| Formulation C | 4.78 ± 0.47 | 0.72 ± 0.76 | 3.08 ± 0.24 | 0.00 ± 0.00 | 3.90 ± 0.38 | 1.53 ± 1.14 |
| Formulation D | 5.08 ± 0.47 | 1.52 ± 1.15 | 3.25 ± 0.30 | 0.14 ± 0.31 | 3.61 ± 0.93 | 0.40 ± 0.59 |
| Excipient | 5.85 ± 0.22 | 4.79 ± 0.39 | 5.32 ± 0.88 | 2.02 ± 1.23 | 4.89 ± 0.45 | 3.86 ± 0.53 |
| No treatment ctrl | 7.58 ± 0.12 | 7.23 ± 0.37 | 8.79 ± 0.02 | 8.65 ± 0.08 | 7.17 ± 0.06 | 5.98 ± 0.25 |

The efficacy of tissue repair formulations against 3-day-old biofilms of methicillin-resistant *S. aureus* is summarized in FIG. 1. Overall, the Formulations A-D showed comparable efficacy with approximately 5 log survival after 24 h treatment, compared to about 7.5 logs for the untreated controls. Extended treatment time reduced the survival significantly to levels below 1 log for Formulations A-C and about 1.5 logs for Formulation D. Interestingly, the excipient also showed reduction in microbial load at the 24 h treatment mark, almost 2 log reduction, but the extended treatment time decreased the survival of *S. aureus* by only about another 1 log, while the tested Formulations showed significantly higher efficacy.

The efficacy of tissue repair formulations against 3-day-old biofilms of *P. aeruginosa* is summarized in FIG. 2. Similar to what was reported for *S. aureus*, the extended treatment time increased efficacy of all Formulations. Formulations A-D all showed more than 5 log reduction within 24 h and less than 1 log survival after 72 h. These Formulations appear to have better efficacy against *P. aeruginosa* than *S. aureus* at the 24 h treatment time point; however, the excipient alone also showed a time-dependent increase in efficacy against *P. aeruginosa* biofilms, with the 72 h treatment time resulting in 2 log survival.

The efficacy of tissue repair Formulations against 3-day old biofilms of *C. albicans* is summarized in FIG. 3. The overall efficacy profile against *C. albicans* is similar to that observed for the Gram positive *S. aureus* where all of the Formulations show an increase in efficacy with extended treatment time (72 h vs 24 h treatment), and the efficacy at the 72 h treatment time point is significantly higher than that of the excipient alone.

Overall, all of the Formulations evaluated in the study showed very high efficacy against biofilms from all three representative microbial species evaluated: Gram positive *S. aureus*, Gram negative *P. aeruginosa* and yeast *C. albicans*. The extended treatment time of 72 h resulted in an overall increase in efficacy for all Formulations, resulting in ≤1.5 logs of viable bacteria across all species. The excipient alone also showed a decrease in microbial load with about 2-3 log reduction after 24 h and 72 h treatment times for *S. aureus* and *C. albicans*, and 3 log reduction at 24 h and almost 7 log reduction at 72 h for *P. aeruginosa*.

There are a few important things to note here that may be relevant for explaining the observed excipient efficacy:

Total microbial load was enumerated in this study, biofilm+planktonic bacteria.

This might explain partial efficacy of the excipient, especially for 24 h treatment. As a reference, if 3-day old explants with biofilm are treated for 24 h in a solution of antibiotic or an antifungal agent at concentrations >200× the MIC value, in general we see a reduction of microbial load by ≤2 logs.

*P. aeruginosa* produces biofilms with a lot more biomass than other species. If the components of the excipient are disrupting the *P. aeruginosa* biofilm, this can result in increase in observed efficacy, though it may come not from microbial killing, rather from the physical removal of the biofilms from the tissue.

Example 7: Assessment of Wound Healing in Full Thickness Excisional Porcine Model with Hydrogel Formulations Containing Anti-Biofilm Inhibitors This example describes evaluation of four tissue healing hydrogel formulations containing different concentrations of propolis, baicalin and andrographolide in a porcine full thickness excisional wound healing dermal model.

The healing properties of the tissue repair hydrogels (e.g., hydrogels comprising propolis) and three predicates on full thickness skin wounds were studied in a porcine model. One male pig (Large white) weighing about 39.5 kg were acclimatized for 3 days and prior to surgery and fasted for 12 h. The animal was sedated with intramuscular ketamine (5 mg/kg), midazolam (0.5 mg/kg) and acepromazine (0.05 mg/kg). After sedation the animal was anesthetized by auricular intravenous injection of Propofol (5 mg/kg) following isoflurane inhalation to maintain the sedation. Anesthetic block was performed at the incision site with lidocaine 2%. Before surgery, the dorsal surface was shaved and sterilized with chlorhexidine 2%. 16 full thickness incisional wounds with a diameter of 2 cm were made symmetrically in four rows by scalp N.11 and scissors on the back of the pig using a stainless-steel template.

Figure 4:
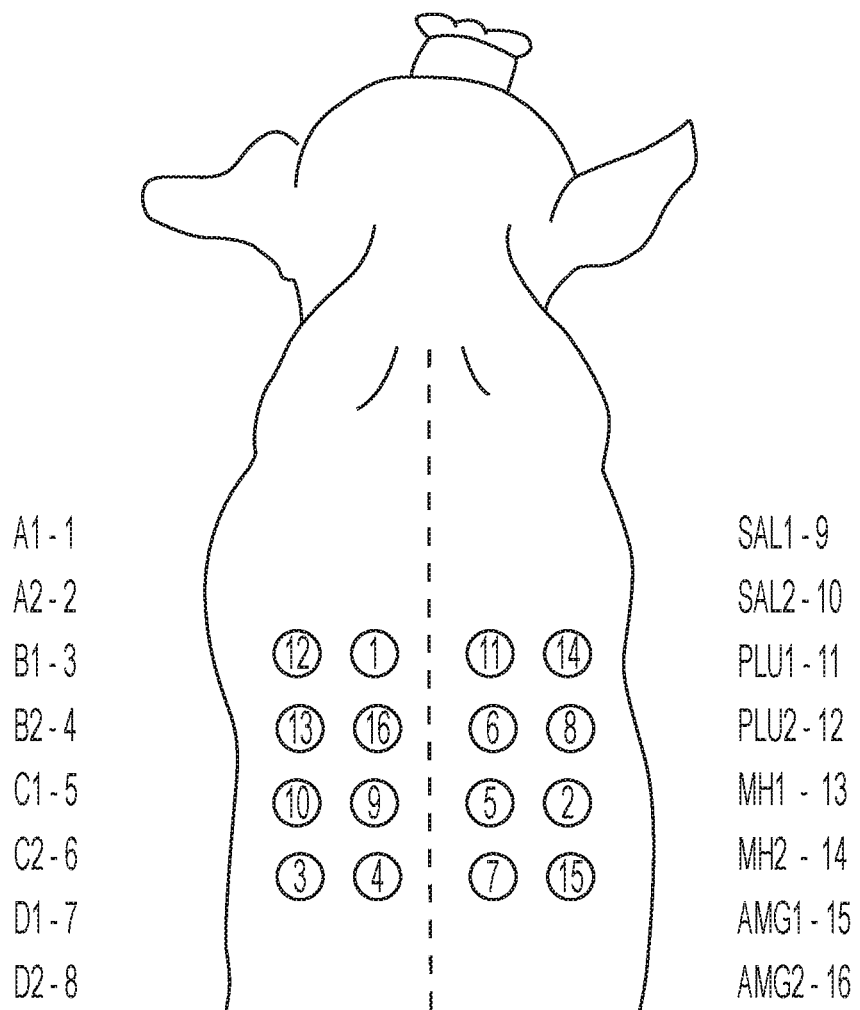
FIG. 4 shows a schematic depicting wound sites on pig dorsal region randomly selected for each treatment.

Eight tissue healing treatments in duplicate were tested on the wound sites: InnovaCorium Dressing Hydrogel (IWD)—Formulation A, B, C and D, Plurogel® (PG—Medline, Northfield, IL), Medihoney® (MH—Derma Sciences, Toronto, Canada), Amerigel® (AMG—Amerx, Clearwater, FL) and saline control (SAL). The sites were randomly selected for each treatment according to FIG. 4. Amounts of selected components in Formulations A, B, C, and D are shown in Table 8 below.

TABLE 8

| Formulation | Propolis (% w/w) | Baicalin (% w/w) | Andrographolide (% w/w) |
|---|---|---|---|
| A | 3.0% | 1% | 1% |
| B | 1.5% | 0.5% | 0.5% |
| C | 0.75% | 0.25% | 0.25% |
| D | 6% | 0.5% | 0.5% |

An amount of 0.5 g of each product were administrated on the wound bed every 24 hours during the 22 days of the study. The wounds were initially rinsed with sterile saline to remove product residues from the previous application. Then the peri-wound region was wiped with sterile gauze for better fixation of the new dressing cover. To reduce the stress and pain of the animal during the dressing changes, a sedation of intramuscular Ketamine (10 mg/kg) and Midazolam (0.5 mg/kg) was administrated for the first week. The wound sites were covered by a Curatec transparent film (Urgo Medical, France) and with 3M™ Micropore™ Surgical Tape (3M, Maplewood, MN). After covering the lesions, the animal was dressed in a clean cotton garment for better comfort and protection from occasional trauma.

To assess the treatment wound healing efficacy the wounds were photographed every week to estimate the area using the Image J software (NIH, USA) with a known circular area template as a reference. Biopsies from the wound bed were collected at day 15 (Replicate 1) and day 22 (Replicate 2) to evaluate the histological healing stage of the wounds. The histological slides were made with 3 micrometer sections and then left for 30 minutes in a 75° C. oven to drain the paraffin. Hematoxylin/eosin and Masson's Trichrome stains were used. Briefly, samples were deparaffinized in 3 xylol vats for 5 min each, then hydrated with 10 passes in decreasing alcohol, 100%, 90%, 80%, 70% and water. Nuclear staining was done with Harrys Hematoxylin for 3 min followed by Washing in running water for 1 min. Hematoxylin tiling performed by 10 passes in Scoth solution and rinsing in running water for an additional 2 min. The cytoplasm was stained by Eosin for 3 min. Finally, the dehydration made by increasing alcohols and clarification by 3 xylol vats 10 passages in each one for the assembly in synthetic medium. Massom trychomic staining was performed by deparaffinization in 3 xylol vats 5 minutes each and staining with hematoxylin for 3 min. Samples were tiled in the Scoth solution for 10 passes. The samples were then subjected to Briebrich Scarlat Solution-15 min, Phosphotungstic Acid/Phosphololybdic-10 min, Aniline Blue-5 min and Acetic Acid 1%-2 min. Dehydration in increasing alcohols, clarification and assembly in synthetic medium.

Figure 5G:
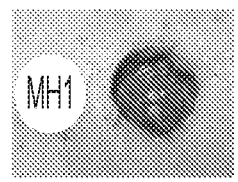
Figure 5G:
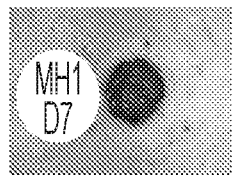
Figure 5G:
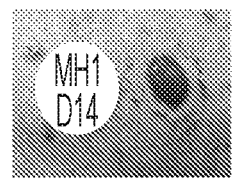
Figure 5G:
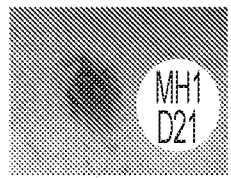
Figure 5G:
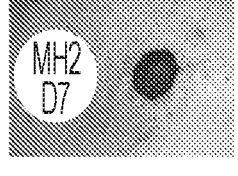
Figure 5G:
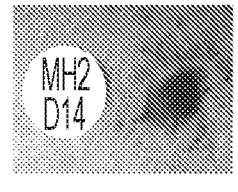
Figure 5G:
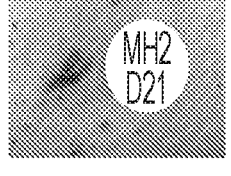
Figure 5H:
Figure 5H:
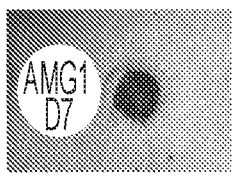
Figure 5H:
Figure 5H:
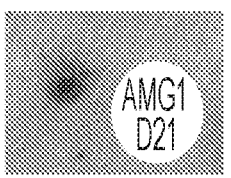
Figure 5H:
Figure 5H:
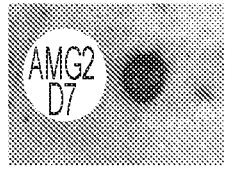
Figure 5H:
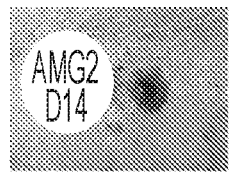
Figure 5H:
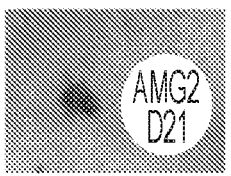
Figure 6:
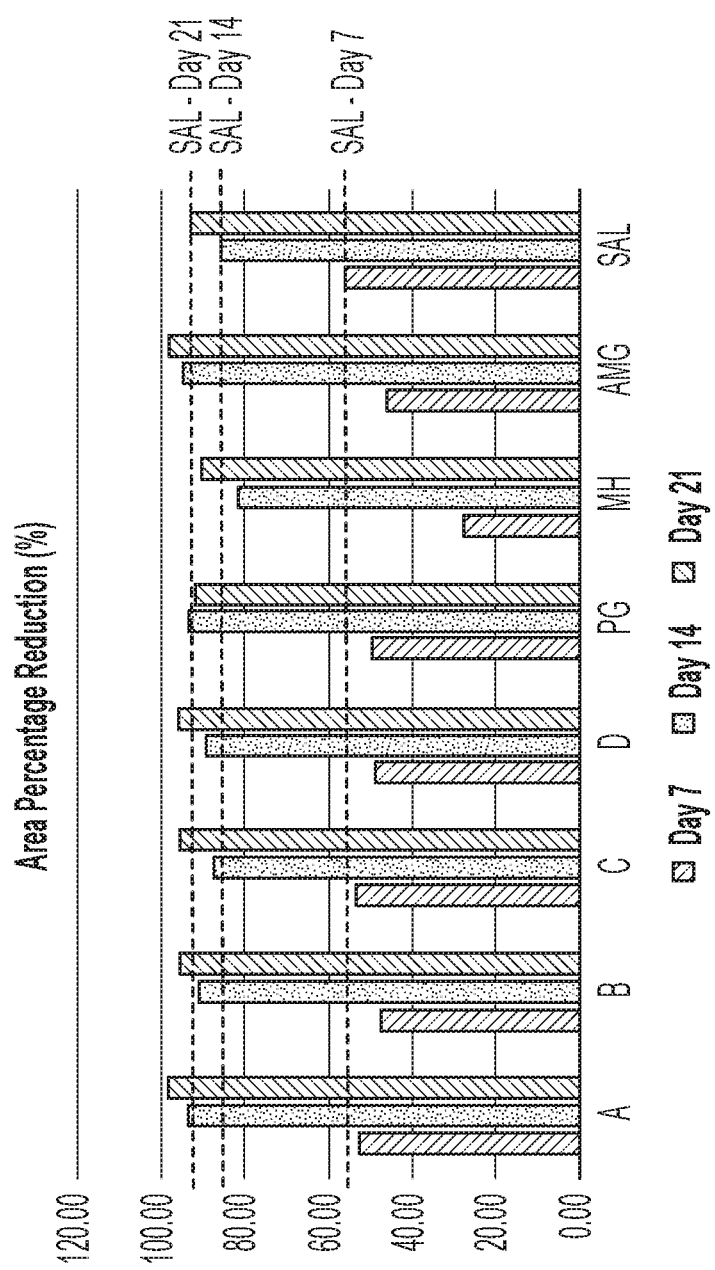
FIG. 6 shows wound area percentage reduction of wound healing composition treatments and saline control. A, Formulation A; B, Formulation B; C, Formulation C; D, Formulation D; PG, Plurogel; MH, Medihoney; AMG; Amerigel; SAL, saline control.

FIGS. 5A-5H are photographs depicting the healing process of full thickness excisional wounds on pig skin with various treatment and control. Twenty-four hours after surgery for the production of excisional wounds, they were clean without signs of bleeding, infections, edema and erythema. After 7 days of treatment, all tissue repair Formulation-treated wounds, regardless of Formulation A, B, C, or D, showed a slight impregnation of product on the wound bed. On the peri-wound region there was slight impregnation of product difficult to rinse with saline. These impregnations were more pronounced in formulations with the highest concentration of propolis (FIGS. 5A and 5D). Wounds treated with different predicates and control saline also had impregnations, but not as dark and thick as in the propolis-containing Formulations. After 14 days of treatment no lesion had more wound bed product accumulation. Among the Formulations, Formulation C presented the largest area of granulation tissue associated with the lowest wound percentage reduction rate (FIG. 5C). One of the MH-treated wounds presented hyper granulation and edema, however, no infection, exudate, and erythema was observed in any of the wounds throughout the study period (FIG. 5G). Data show that in the first week of treatment, there was no significant reduction of the lesion area in any of the treatments compared to saline control. However, in the second week of treatment, each Formulation performed better than the saline control. Table 9 shows the wound area of each treatment and control over the period of observation. By the end of the study, Formulation A shows the highest wound percentage reduction (98.6%), compared to the saline control (93.3%), as shown in FIG. 6. MH treatment did not result in wound healing during this study.

TABLE 9

| Wound Area (mm$^2$) | Baseline | Day 7 | Day 14 | Day 21 |
| --- | --- | --- | --- | --- |
| A | 518.6 ± 98.2 | 244.6 ± 1.6 | 32.8 ± 10.3 | 7.5 ± 10.4 |
| B | 432.7 ± 43.5 | 227.0 ± 75.2 | 39.2 ± 42.6 | 18.0 ± 18.1 |
| C | 554.8 ± 53.8 | 257.0 ± 38.0 | 70.3 ± 1.6 | 23.9 ± 17.6 |
| D | 491.9 ± 95.0 | 250.9 ± 9.9 | 53.7 ± 11.4 | 20.6 ± 29.1 |
| PG | 483.0 ± 50.7 | 243.8 ± 47.8 | 31.7 ± 12.3 | 11.6 ± 12.3 |
| MH | 520.8 ± 6.6 | 377.1 ± 100.9 | 94.6 ± 23.0 | 50.0 ± 52.0 |
| AMG | 409.8 ± 77.4 | 221.9 ± 2.7 | 19.8 ± 3.8 | 8.1 ± 11.4 |
| SAL | 490.4 ± 62.7 | 217.0 ± 22.5 | 71.3 ± 23.5 | 33.1 ± 25.2 |

Histological characteristics of intact porcine skin and all wounds treated with different products were assessed. Biopsies collected from undamaged intact tissue showed a very characteristic dermal structure of porcine integument, with unmodified dense connective tissue with collagen fiber bundles, absence of atypical and/or inflammatory cell infiltrate and few dermal papillae. In general, the observed fragments were fully epithelized with a thin uncompressed keratin layer. Histological sections of biopsies taken from the wounds showed epidermal structures not as organized as intact skin, and mainly characterized by the presence of inflammatory infiltrates and loose connective tissue deposition with sparser and less dense fibers. The biopsies collected from the wounds showed that, in general, the Formulations A and D had a greater tissue turnover in 15 days with epidermis formation with invagination and deposition of keratin by stratified keratinocytes. Formulation C was the longest to arrive at this stage. Among the predicates, AMG was the one that most quickly reconstituted the epidermal and dermal structures. On the other hand, MH product took the longest time to repair the skin layers. After 21 days the histological sections from the biopsies of the tissue repair composition-treated wounds showed complete organization and stratification of the epidermal structures, with the distinction between the different stratum layers of the epidermis, even in lesions treated with Formulation C. On the other hand, wounds treated with MH and SAL had incomplete epidermis formation by the end of 21 days of treatment.

Data described above indicate that all tissue healing formulations (e.g., A, B, C, and D) demonstrated healing effectiveness in porcine full thickness excisional wounds compared to saline-treated lesions. PG and AMG products have also demonstrated healing effectiveness on the test. Formulation A and AMG performed the best, achieving in 21 days wound reduction percentage above 98%. Differences in the healing stages of the porcine excisional wounds between the different treatments and control were histologically followed to confirm tissue reorganization over the skin repair process. Again, Formulation A, Formulation D, and AMG showed advanced epidermis layer restructuring after day 15 of the treatment.

EQUIVALENTS

Having thus described several aspects of at least one embodiment of this invention, it is to be appreciated that various alterations, modifications, and improvements will readily occur to those skilled in the art. Such alterations, modifications, and improvements are intended to be part of this disclosure, and are intended to be within the spirit and scope of the invention. Accordingly, the foregoing description and drawings are by way of example only.

While several embodiments of the present invention have been described and illustrated herein, those of ordinary skill in the art will readily envision a variety of other means and/or structures for performing the functions and/or obtaining the results and/or one or more of the advantages described herein, and each of such variations and/or modifications is deemed to be within the scope of the present invention. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present invention is/are used. Those skilled in the art will recognize, or be able to ascertain using no more than routine experimentation, many equivalents to the specific embodiments of the invention described herein. It is, therefore, to be understood that the foregoing embodiments are presented by way of example only and that, within the scope of the appended claims and equivalents thereto, the invention may be practiced otherwise than as specifically described and claimed. The present invention is directed to each individual feature, system, article, material, and/or method described herein. In addition, any combination of two or more such features, systems, articles, materials, and/or methods, if such features, systems, articles, materials, and/or methods are not mutually inconsistent, is included within the scope of the present invention.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively pres-

What is claimed is:

1. A composition comprising:
   (i) a drug delivery system comprising a carbonate buffer solution, at least two different biosurfactants, at least one hygroscopic agent, and at least one antioxidant; and
   (ii) at least one bioactive agent present at about 0.1% (w/w) to about 4% (w/w), wherein the composition has a pH that ranges from about 8.5 to about 9.5 wherein the at least one bioactive agent is selected from the group consisting of: *Melissa officinalis* extract; propolis;
   baicalin; marine algae powder selected from Enteromorpha linza extract, Ulva *lactuca* extract, *Porphyra* haitanensis, or *Laminaria japonica* extract; aloe vera; carrot oil; and one or more antiviral agent;
   wherein the at least two biosurfactants are rhamnolipid and sophorolipid; and wherein the rhamnolipid and sophorolipid are each present at about 0.01% (w/w) to about 6.5% (w/w);
   wherein the at least one hygroscopic agent is polyethylene glycol;
   wherein polyethylene glycol is present at about 0.1% (w/w) to about 20% (w/w);
   wherein the at least one antioxidant is alpha-tocopherol or butylated hydroxytoluene; and
   wherein the alpha-tocopherol or butylated hydroxytoluene is present at about 0.01% (w/w) to about 2.92% (w/w).

2. The composition of claim 1, wherein:
   the carbonate buffer solution comprises one of the following ions: sodium, potassium, calcium, and magnesium.

3. The composition of claim 1, wherein the composition is formulated as a solid, liquid, gel, or foam.

4. A solid substrate comprising the composition of claim 1.

5. A kit comprising
   the composition of claim 1.

6. The kit of claim 5, wherein the one or more antiviral agents is selected from acyclovir, valacyclovir and famciclovir, and/or the herpes simplex virus is Herpes simplex labialis (HSL).

7. The composition of claim 1, wherein the carbonate buffer solution is sodium bicarbonate buffer solution.

8. The composition of claim 1, wherein the ratio of rhamnolipid to sophorolipid is about 1:1 or about 7:3.

9. The composition of claim 3, wherein the solid is a powder.

10. The composition of claim 9, wherein the powder is a lyophilized powder.

11. The composition of claim 3, wherein the composition is present on or in a solid substrate and the solid substrate comprises cotton fibers.

12. The composition of claim 3, wherein the liquid is a mouthwash; the gel is a hydrogel; and/or the foam is formulated as an aerosolized spray.

13. The composition of claim 1, wherein the *Melissa officinalis* extract further comprises one or more vitamin B complex.

14. The composition of claim 13, wherein the one or more B vitamin complexes is dexpanthenol.

15. The composition of claim 11, wherein the solid substrate is a bandage or a cotton mask.

* * * * *